(12) United States Patent
Jelcic et al.

(10) Patent No.: US 9,738,690 B2
(45) Date of Patent: Aug. 22, 2017

(54) POLYOMA VIRUS JC PEPTIDES AND PROTEINS IN VACCINATION AND DIAGNOSTIC APPLICATIONS

(75) Inventors: Ilijas Jelcic, Zurich (CH); Roland Martin, Zurich (CH); Sven Schippling, Zurich (CH); Mireia Sospedra, Zurich (CH); Sara Yousef, Hamburg (DE)

(73) Assignee: UNIVERSITAET ZUERICH, Zurich (CH)

(*) Notice: Subject to any disclaimer, the term of this patent is extended or adjusted under 35 U.S.C. 154(b) by 0 days.

(21) Appl. No.: 14/234,065

(22) PCT Filed: Jul. 23, 2012

(86) PCT No.: PCT/EP2012/064445
§ 371 (c)(1),
(2), (4) Date: Aug. 20, 2014

(87) PCT Pub. No.: WO2013/014134
PCT Pub. Date: Jan. 31, 2013

(65) Prior Publication Data
US 2014/0356320 A1 Dec. 4, 2014

(30) Foreign Application Priority Data

Jul. 22, 2011 (EP) .................................. 11006031

(51) Int. Cl.
| | | |
|---|---|---|
| C12Q 1/70 | (2006.01) | |
| C07K 14/005 | (2006.01) | |
| A61K 39/12 | (2006.01) | |
| A61K 38/20 | (2006.01) | |
| C07K 7/08 | (2006.01) | |
| A61K 38/16 | (2006.01) | |
| A61K 38/00 | (2006.01) | |
| C12N 7/00 | (2006.01) | |
| A61K 39/00 | (2006.01) | |

(52) U.S. Cl.
CPC ........ *C07K 14/005* (2013.01); *A61K 38/2046* (2013.01); *A61K 39/12* (2013.01); *C07K 7/08* (2013.01); *C12Q 1/70* (2013.01); *A61K 38/00* (2013.01); *A61K 38/162* (2013.01); *A61K 2039/55511* (2013.01); *A61K 2039/55527* (2013.01); *C12N 7/00* (2013.01); *C12N 2710/22022* (2013.01); *C12N 2710/22023* (2013.01); *C12N 2710/22034* (2013.01); *C12N 2710/22071* (2013.01)

(58) Field of Classification Search
CPC ............ C07K 7/08; C12N 2710/22023; C12N 2710/20023; C12N 2730/10123; G01N 33/505
See application file for complete search history.

(56) References Cited

U.S. PATENT DOCUMENTS

| | | | | |
|---|---|---|---|---|
| 6,238,859 B1 * | 5/2001 | Luke | ................... | C07K 14/005 435/235.1 |
| 2003/0044961 A1 | 3/2003 | Luke et al. | | |
| 2004/0259767 A1 | 12/2004 | Nagashima et al. | | |
| 2007/0026503 A1 | 2/2007 | Lacey | | |
| 2008/0057079 A1 | 3/2008 | Boland | | |
| 2009/0099335 A1 | 4/2009 | Lacey | | |
| 2012/0034249 A1 | 2/2012 | June et al. | | |
| 2012/0258443 A1 | 10/2012 | Gorelik et al. | | |

FOREIGN PATENT DOCUMENTS

| | | |
|---|---|---|
| DE | 19543553 A1 | 5/1997 |
| JP | 9-67397 A | 3/1997 |
| JP | 2000-500973 A | 2/2000 |
| JP | 2003-61693 A | 3/2003 |
| JP | 2005-341864 | 12/2005 |
| JP | 2005-341864 A | 12/2005 |
| WO | 03/106626 A2 | 12/2003 |
| WO | WO 2008/091398 A2 | 7/2008 |
| WO | WO 2010/090757 A1 | 8/2010 |
| WO | 2010/100182 A1 | 9/2010 |
| WO | WO 2010/099205 A1 | 9/2010 |
| WO | 2011/124652 A1 | 10/2011 |

OTHER PUBLICATIONS

Du Pasquier et al (Journal of Virology 77:11918-26, 2003).*
Black et al. J. B. Cm 1992, vol. 267, No. 14, pp. 9743-9748.*
Wu et al. J. Virol. 2006, vol. 80, No. 22, pp. 11393-11397.*
Miki et al. J. B. C. 1999, vol. 274, No. 41, pp. 29057-29062).*
Norton Carol by 2015 Multiple Sclerosis Discovery Forum, pp. 1-5.*
Diotti et al. Virology, 2016, vol. 128, pp. 107, please see pp. 1 and 7).*
International Preliminary Report on Patentability and Written Opinion for Application No. PCT/EP2012/064445, 13 pages, dated Jan. 18, 2014.
Clark, Tristan W. et al., "Trial of 2009 Influenza A (H1N1) Monovalent MF59-Adjuvanted Vaccine," The New England Journal of Medicine, vol. 361:2424-2435 (2009).
Cytheris SA, "Cytheris Announces Publication of Clinical Case Study Combining Recombinant Human Interleukin-7 (CYT107) with Antiviral Agent CMX001 as Potential Treatment for Progressive Multifocal Leukoencephalopathy (PML)," http://www.businesswire.com/news/home/20101130005169/en/Cytheris-Announces-Publication-Clinical-Case-Study-Combining, 4 pages (2010).
Frisque, Richard J. et al., "Human Polyomavirus JC Virus Genome," Journal of Virology, vol. 51(2):458-469 (1984).

(Continued)

*Primary Examiner* — Bao Li
(74) *Attorney, Agent, or Firm* — Norman B. Thot

(57) ABSTRACT

The present invention relates to the field of vaccination or immunization, in particular therapeutic vaccination, and diagnosis. Pharmaceutical compositions and kits capable of eliciting a protective immune response against polyoma virus JC (JCV) are disclosed, which may be used e.g., for therapy or for prevention of progressive multifocal leukoencephalopathy (PML) and/or progressive multifocal leukoencephalopathy-immune reconstitution inflammatory syndrome (PML-IRIS). Individuals in danger of such PML or PML-IRIS may, e.g., be immuno-compromised or immunosuppressed patients or patients having an autoimmune disease eligible for immunosuppressive treatment. The invention also relates to compositions comprising at least one CD4+ epitope of a JCV protein and to therapeutic, prophylactic and diagnostic uses thereof.

13 Claims, 10 Drawing Sheets

(56) References Cited

OTHER PUBLICATIONS

Figure 1:
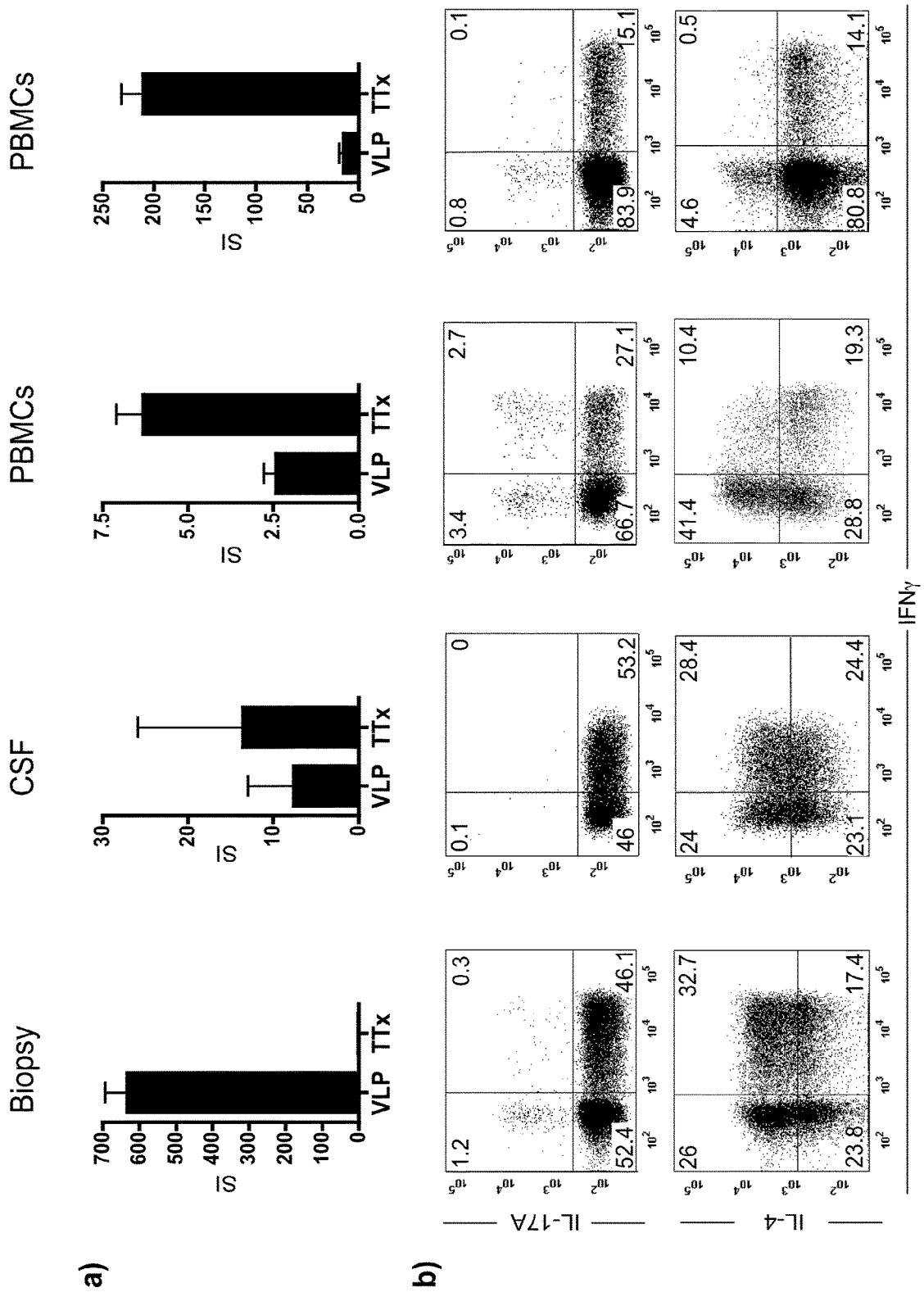

Gasnault, Jacques et al., "Critical role of JC virus-specific CD4 T-cell responses in preventing progressive multifocal leukoencephalopathy," AIDS, vol. 17:1443-1449 (2003).
Gheuens, Sarah et al., "Role of CD4+ and CD8+ T-Cell Responses against JC Virus in the Outcome of Patients with Progressive Multifocal Leukoencephalopathy (PML) and PML with Immune Reconstitution Inflammatory Syndrome," Journal of Virology, vol. 85(14):7256-7263 (2011).
Koralnik, Igor J., "Overview of the cellular immunity against JC virus in progressive multifocal leukoencephalopathy," Journal of NeuroVirology, vol. 8(Suppl. 2):59-65 (2002).
Moniuszko, Marcin et al., "Recombinant Interleukin-7 Induces Proliferation of Naive Macaque CD4+ and CD8+ T Cells In Vivo," Journal of Virology, vol. 78(18):9740-9749 (2004).
Patel, Amila et al., "Treatment of progressive multifocal leukoencephalopathy and idiopathic CD4+ lymphocytopenia," Journal of Antimicrobial Chemotherapy, vol. 65:2489-2492 (2010).
Rechsteiner, Gerd et al., "Cutting Edge: Priming of CTL by Transcutaneous Peptide Immunization with lmiquimod," The Journal of Immunology, vol. 174:2476-2480 (2005).
Shishido-Hara, Yukiko et al., "Analysis of Capsid Formation of Human Polymavirus JC (Tokyo-1 Strain) by a Eukaryotic Expression System: Splicing of Late RNAs, Translation and Nuclear Transport of Major Capsid Protein VP1, and Capsid Assembly," Journal of Virology, vol. 74(4):1840-1853 (2000).
Shishido-Hara, Yukiko et al., "Major and Minor Capsid Proteins of Human Polymavirus JC Cooperatively Accumulate to Nuclear Domain 10 for Assembly into Virions," Journal of Virology, vol. 78(18):9890-9903 (2004).
Tan, Chen S. et al., "Beyond progressive multifocal leukoencephalopathy: expanded pathogenesis of JC virus infection in the central nervous system," Lancet Neurol., vol. 9(4):425-467 (2010).
International Search Report for Application No. PCT/EP2012/064445, 7 pages, dated Mar. 1, 2013.
Aly, Lilian et al., "Central role of JC virus-specific CD4+ lymphocytes in progressive multi-focal leucoencephalopathy-immune reconstitution inflammatory syndrome," Brain, vol. 134:2687-2702 (2011).
Astrom, Karl-Erik et al., "Progressive Multifocal Leuko-encephalopathy. A Hitherto Unrecognized Complication of Chronic Lymphatic Leukemia and Hodgkin's Disease," Brain, vol. 81(1):93-111 (1958).
Carreno, Beatriz M. et al., "Overlapping Epitopes that Are Recognized by CD8+ HLA Class I-Restricted and CD4+ Class II-Restricted Cytotoxic T Lymphocytes Are Contained within an Influenza Nucleoprotein Peptide," The Journal of Immunology, vol. 148(3):894-899 (1992).
Cavacini, Lisa A. et al., "Binding and Neutralization Activity of Human IgG1 and IgG3 from Serum of HIV-Infected Individuals," Aids Research and Human Retroviruses, vol. 19(9):785-792 (2003).
Cinque, Paola et al., "The effect of highly active antiretroviral therapy-induced immune reconstitution on development and outcome of progressive multifocal leukoencephalopathy: Study of 43 cases with review of the literature," Journal of NeuroVirology, vol. 9(Suppl. 1):73-80 (2003).
Du Pasquier, Renaud A. et al., "A prospective study demonstrates an association between JC virus-specific cytotoxic T lymphocytes and the early control of progressive multifocal leukoencephalopathy," Brain, vol. 127:1970-1978 (2004).
Du Pasquier, Renaud A. et al., "Detection of JC Virus-Specific Cytotoxic T Lymphocytes in Healthy Individuals," Journal of Virology, vol. 78(18):10206-10210 (2004).
Du Pasquier, Renaud A. et al., "JC virus induces a vigorous CD8+ cytotoxic T cell response in multiple sclerosis patients," Journal of Neuroimmunology, vol. 176:181-186 (2006).
Du Pasquier, Renaud A. et al., "JCV-specific cellular immune response correlates with a favorable clinical outcome in HIV-infected individuals with progressive multifocal leukoencephalopathy," Journal of NeuroVirology, vol. 7:318-322 (2001).
Du Pasquier, Renaud A. et al., "Low Frequency of Cytotoxic T Lymphocytes against the Novel HLA-A *0201-Restricted JC Virus Epitope VP1p36 in Patients with Proven or Possible Progressive Multifocal Leukoencephalopathy," Journal of Virology, vol. 77(22):11918-11926 (2003).
Du Pasquier, R.A. et al., "Productive infection of cerebrellar granule cell neurons by JC virus in an HIV+ individual," Neurology, vol. 61:775-782 (2003).
Egli, Adrian et al., "Prevalence of POlymavirus BK and JC Infection and Replication in 400 Healthy Blood Donors," The Journal of Infectious Diseases, vol. 199:837-846 (2009).
Gasnault, Jacques et al., "Improved Survival of HIV-1-Infected Patients with Progressive Multifocal Leukoencephalopathy Receiving Early 5-Drug Combination Antiretroviral Therapy," PLoS One, vol. 6(6):e20967, 11 pages (2011).
Gillespie, Sheila M. et al., "Progressive Multifocal Leukoencephalopathy in Persons Infected with Human Immunodeficiency Virus, San Francisco, 1981-1989," Ann. Neurol., vol. 30:597-604 (1991).
Goldmann, Claudia et al., "Molecular Cloning and Expression of Major Structural Protein VP1 of the Human Polyomavirus JC Virus: Formation of Virus-Like Particles Useful for Immunological and Therapeutic Studies," Journal of Virology, vol. 73(5):4465-4469 (1999).
Hegazy, Ahmed N. et al., "Interferons Direct Th2 Cell Reprogramming to Generate a Stable GATA-3+T-bet+ Cell Subset with Combined Th2 and Th1 Cell Functions," Immunity, vol. 32:116-128 (2010).
Houff, Sidney A. et al., "Involvement of JC Virus-Infected Mononuclear Cells from the Bone Marrow and Spleen in the Pathogenesis of Progressive Multifocal Leukoencephalopathy," The New England Journal of Medicine, vol. 318 (5):301-305 (1988).
Jilek, Samantha et al., "Immune responses to JC virus in patients with multiple sclerosis treated with natalizumab: a cross-sectional and longitudinal study," Lancet Neurol., vol. 9(3):264-272 (2010).
Kleinschmidt-Demasters, B.K. et al., "Progressive Multifocal Leukoencephalopathy Complicating Treatment with Natalizumab and Interferon Beta-1a for Multiple Sclerosis," The New England Journal of Medicine, vol. 353:369-374 (2005).
Koralnik, Igor J. et al., "Association of Prolonged Survival in HLA-A2+ Progressive Multifocal Leukoencephalopathy Patients with a CTL Response Specific for a Commonly Recognized JC Virus Epitope," The Journal of Immunology, vol. 168:499-504 (2002).
Koralnik, Igor J. et al., "JC Virus-Specific Cytotoxic T Lymphocytes in Individuals with Progressive Multifocal Leukoencephalopathy," Journal of Virology, vol. 75(7):3483-3487 (2001).
Koralnik, Igor J., "Progressive Multifocal Leukoencephalopathy Revisited: Has the Disease Outgrown Its Name?" Ann. Neurol., vol. 60:162-173 (2006).
Langer-Gould, Annette et al., "Progressive Multifocal Leukoencephalopathy in a Patient Treated with Natalizumab," The New England Journal of Medicine, vol. 353:375-381 (2005).
Li, Jongming et al., "Characterization of Non-Conserved HLA-A*0201 Binding T cell Epitopes of JC Virus T Antigen," Virology: Research and Treatment, vol. 1:87-95 (2008).
Li, Jongming et al., "T-cell responses to peptide fragments of the BK virus T antigen: implications for cross-reactivity of immune response to JC virus," Journal of General Virology, vol. 87:2951-2960 (2006).
Major, Eugene O., "Progressive Multifocal Leukoencephalopathy in Patients on Immunomodulatory Therapies," Annu. Rev. Med., vol. 61:35-47 (2010).
Ogg, Graham S. et al., "Quantitation of HIV-1-Specific Cytotoxic T Lymphocytes and Plasma Load of Viral RNA," Science, vol. 279(5359):2103-2106 (1998).
Padgett, Billie L. et al. "Cultivation of Papova-like Virus from Human Brain with Progressive Multifocal Leucoencephalopathy," The Lancet, vol. 1(7712):1257-1260 (1971).

(56) References Cited

OTHER PUBLICATIONS

Patel, Amila et al., "A case of progressive multifocal leukoencephalopathy and idiopathic CD4+ lymphocytopenia," J. Antimicrob. Chemother., vol. 65(12):2697-2698 (2010).
Ransohoff, Richard M., "Natalizumab and PML," Nature Neuroscience, vol. 8(10):1275 (2005).
Stoner, Gerald L. et al., "JC papovavirus large tumor (T)-antigen expression in brain tissue of acquired immune deficiency syndrome (AIDS) and non-AIDS patients with progressive multifocal leukoencephalopathy," Proc. Natl. Acad. Sci. USA, vol. 83:2271-2275 (1986).
Stuve, Olaf et al., "Immune Surveillance in Multiple Sclerosis Patients Treated with Natalizumab," Ann. Neurol., vol. 59:743-747 (2006).
Tan, Chen S. et al., "Detection of JC Virus DNA and Proteins in the Bone Marrow of HIV-Positive and HIV-Negative Patients: Implications for Viral Latency and Neurotropic Transformation," The Journal of Infectious Diseases, vol. 199:881-888 (2009).
Tan, K. et al., "PML-IRIS in patients with HIV infection. Clinical manifestations and treatment with steroids," Neurology, vol. 72:1458-1464 (2009).
Tan, Chen S. et al., "Progressive multifocal leukoencephalopathy and other disorders caused by JC virus: clinical features and pathogenesis," Lancet Neurol., vol. 9(4):425-437 (2010).
Weber, Thomas et al., "Analysis of the Systemic and Intrathecal Humoral Immune Response in Progressive Multifocal Leukoencephalopathy," The Journal of Infectious Diseases, vol. 176:250-254 (1997).
Zhou, Wendi et al., "Functional Characterization of BK Virus-Specific CD4+ T Cells with Cytotoxic Potential in Seropositive Adults," Viral Immunology, vol. 20(3):379-388 (2007).
Zhu, Jinfang et al., "CD4+ T Cell Plasticity—Th2 Cells Join the Crowd," Immunity, vol. 32(1):11-13 (2010).
Zhu, Jinfang et al., "Differentiation of Effector CD4 T Cell Populations," Ann. Rev. Immunol., vol. 28:445-489 (2010).
Zonios, Dimitrios I. et al., "Idiopathic CD4+ lymphocytopenia: natural history and prognostic factors," Blood, vol. 112 (2):287-294 (2008).
Zu Rhein, Gabriele M. et al., "Particles Resembling Papova Viruses in Human Cerebral Demyelinating Disease," Science, vol. 148(3676)1477-1479 (1965).
European Search Report for Application No. 11006031.6, 11 pages, dated Jan. 9, 2012.
C. S. Tan et al.: "Progressive multifocal leukoencephalopathy and other disorders caused by JC virus: clinical features and pathogenesis", Lancet Neurology, vol. 9, pp. 425-437 (2010).
A. Patel et al.: "Treatment of progressive multifocal leucoencephalopathy and idiopathic CD4+ lymphocytopenia", Journal of Antimicrobial Chemotherapy, vol. 65, pp. 2489-2492 (2010).
M. Moniuszko et al.: "Recombinant Interleukin-7 Induces Proliferation of Naive Macaque CD4$^+$ and CD8$^+$ T Cells In Vivo", Journal of Virology, vol. 78, No. 18, pp. 9740-9749 (2004).
"Cytheris Announces Publication of Clinical Case Study Combining Recombinant Human Interleukin-7 (CYT107) with Antiviral Agent CMX001 as Potential Treatment for Progressive Multifocal Leukoencephalopathy (PML)", Cytheris SA, Cytheris the Immune Enhancing Company, pp. 1-3 (Nov. 30, 2010, Retrieved on May 17, 2016).
A. Balduzzi et al: "Polyomavirus JC-targeted T-cell therapy for progressive multiple leukoencephalopathy in a hematopoietic cell transplantation recipient", Bone Marrow Transplantation, vol. 46, pp. 987-992 (2011).
S. Katona et al.: "JCV vaccination could reduce the risk of developing cognitive decline, dementia, strokes and brain tumors, by preventing chronic JCV cerebral infection, and recurrent reactivation", Medical Hypotheses, vol. 73, pp. 268-269 (2009).
J. Li et al.: "T-cell responses to peptide fragments of the BK virus T antigen: implications for cross-reactivity of immune response to JC virus", Journal of General Virology, vol. 87, pp. 2951-2960 (2006).

* cited by examiner

Fig. 5

| Date | Label | | | | |
|---|---|---|---|---|---|
| 07.03.11 | M -1 | | | MRI | VL |
| 05.04.11 | D -2 | IL-7 | | | |
| 07.04.11 | D 0 | | VP1 | | |
| 09.04.11 | D +2 | | | MRI | |
| 12.04.11 | D +5 | IL-7 | | | VL |
| 19.04.11 | D +12 | IL-7 | VP1 | MRI | VL |
| 03.05.11 | W +4 | | | MRI | |
| 18.05.11 | W +6 | IL-7 | VP1 | MRI | VL |
| 27.06.11 | M +3 | | | MRI | VL |

-●- Viral load (DNA copies/ml)   -■- Proliferation after VP1 stimulation

-●- Viral load (DNA copies/ml)   -■- Leukocytes in CSF (cells/μl)

on April 5, 12, and 12, 2011     on April 7 and 20, 2011

Fig. 11
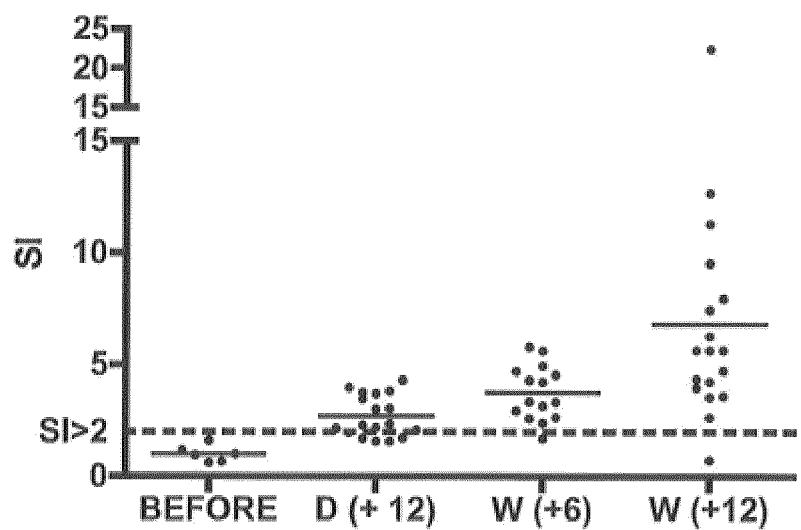
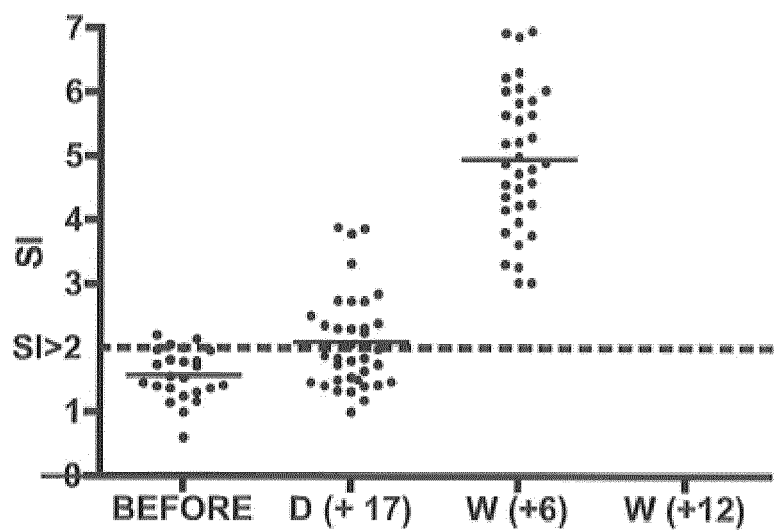

SEQUENCE LISTING

```
<160> NUMBER OF SEQ ID NOS: 92

<210> SEQ ID NO 1
<211> LENGTH: 15
<212> TYPE: PRT
<213> ORGANISM: JC virus

<400> SEQUENCE: 1

Ala Gln Arg Ile Leu Ile Phe Leu Leu Glu Phe Leu Leu Asp Phe
1               5                   10                  15
```

```
<210> SEQ ID NO 2
<211> LENGTH: 15
<212> TYPE: PRT
<213> ORGANISM: JC virus

<400> SEQUENCE: 2

Val Asp Ser Ile Thr Glu Val Glu Cys Phe Leu Thr Pro Glu Met
1               5                   10                  15

<210> SEQ ID NO 3
<211> LENGTH: 15
<212> TYPE: PRT
<213> ORGANISM: JC virus

<400> SEQUENCE: 3

His Leu Arg Gly Phe Ser Lys Ser Ile Ser Ile Ser Asp Thr Phe
1               5                   10                  15

<210> SEQ ID NO 4
<211> LENGTH: 15
<212> TYPE: PRT
<213> ORGANISM: artificial
<220> FEATURE:
<223> OTHER INFORMATION: variant of JCV peptide

<400> SEQUENCE: 4

Ile Ser Asp Thr Phe Glu Ser Asp Ser Pro Asn Arg Asp Met Leu
1               5                   10                  15

<210> SEQ ID NO 5
<211> LENGTH: 15
<212> TYPE: PRT
<213> ORGANISM: artificial
<220> FEATURE:
<223> OTHER INFORMATION: variant of JCV peptide

<400> SEQUENCE: 5

Ile Ser Asp Thr Phe Glu Ser Asp Ser Pro Asn Phe Asp Met Leu
1               5                   10                  15

<210> SEQ ID NO 6
<211> LENGTH: 15
<212> TYPE: PRT
<213> ORGANISM: artificial
<220> FEATURE:
<223> OTHER INFORMATION: variant of JCV peptide

<400> SEQUENCE: 6

Ile Ser Asp Thr Phe Glu Ser Asp Ser Pro Asn Lys Asp Met Leu
1               5                   10                  15

<210> SEQ ID NO 7
<211> LENGTH: 15
<212> TYPE: PRT
<213> ORGANISM: artificial
<220> FEATURE:
<223> OTHER INFORMATION: variant of JCV peptide

<400> SEQUENCE: 7

Asn Arg Asp Met Leu Pro Cys Tyr Ser Val Ala Arg Ile Pro Leu
1               5                   10                  15

<210> SEQ ID NO 8
<211> LENGTH: 15
<212> TYPE: PRT
```

```
<213> ORGANISM: artificial
<220> FEATURE:
<223> OTHER INFORMATION: variant of JCV peptide

<400> SEQUENCE: 8

Asn Phe Asp Met Leu Pro Cys Tyr Ser Val Ala Arg Ile Pro Leu
1               5                   10                  15

<210> SEQ ID NO 9
<211> LENGTH: 15
<212> TYPE: PRT
<213> ORGANISM: artificial
<220> FEATURE:
<223> OTHER INFORMATION: variant of JCV peptide

<400> SEQUENCE: 9

Asn Lys Asp Met Leu Pro Cys Tyr Ser Val Ala Arg Ile Pro Leu
1               5                   10                  15

<210> SEQ ID NO 10
<211> LENGTH: 15
<212> TYPE: PRT
<213> ORGANISM: JC virus

<400> SEQUENCE: 10

Tyr Ser Val Ala Arg Ile Pro Leu Pro Asn Leu Asn Glu Asp Leu
1               5                   10                  15

<210> SEQ ID NO 11
<211> LENGTH: 15
<212> TYPE: PRT
<213> ORGANISM: JC virus

<400> SEQUENCE: 11

Leu Asn Glu Asp Leu Thr Cys Gly Asn Ile Leu Met Trp Glu Ala
1               5                   10                  15

<210> SEQ ID NO 12
<211> LENGTH: 15
<212> TYPE: PRT
<213> ORGANISM: JC virus

<400> SEQUENCE: 12

Leu Met Trp Glu Ala Val Thr Leu Lys Thr Glu Val Ile Gly Val
1               5                   10                  15

<210> SEQ ID NO 13
<211> LENGTH: 15
<212> TYPE: PRT
<213> ORGANISM: JC virus

<400> SEQUENCE: 13

Leu Lys Thr Glu Val Ile Gly Val Thr Ser Leu Met Asn Val His
1               5                   10                  15

<210> SEQ ID NO 14
<211> LENGTH: 15
<212> TYPE: PRT
<213> ORGANISM: artificial
<220> FEATURE:
<223> OTHER INFORMATION: variant of JCV peptide

<400> SEQUENCE: 14

Leu Lys Thr Glu Val Ile Gly Val Thr Thr Leu Met Asn Val His
1               5                   10                  15
```

```
<210> SEQ ID NO 15
<211> LENGTH: 15
<212> TYPE: PRT
<213> ORGANISM: artificial
<220> FEATURE:
<223> OTHER INFORMATION: variant of jcv peptide

<400> SEQUENCE: 15

Leu Lys Thr Glu Val Ile Gly Val Thr Ala Leu Met Asn Val His
1               5                   10                  15

<210> SEQ ID NO 16
<211> LENGTH: 12
<212> TYPE: PRT
<213> ORGANISM: artificial
<220> FEATURE:
<223> OTHER INFORMATION: variant of jcv peptide

<400> SEQUENCE: 16

Leu Met Asn Val His Ser Asn Gly Gln Ala Thr His
1               5                   10

<210> SEQ ID NO 17
<211> LENGTH: 12
<212> TYPE: PRT
<213> ORGANISM: artificial
<220> FEATURE:
<223> OTHER INFORMATION: variant of jcv peptide

<400> SEQUENCE: 17

Leu Met Asn Val His Ser Asn Gly Gln Ala Ala His
1               5                   10

<210> SEQ ID NO 18
<211> LENGTH: 12
<212> TYPE: PRT
<213> ORGANISM: artificial
<220> FEATURE:
<223> OTHER INFORMATION: variant of JCV peptide

<400> SEQUENCE: 18

Leu Met Asn Val His Ser Asn Gly Gln Ala Ser His
1               5                   10

<210> SEQ ID NO 19
<211> LENGTH: 15
<212> TYPE: PRT
<213> ORGANISM: artificial
<220> FEATURE:
<223> OTHER INFORMATION: variant of JCV peptide

<400> SEQUENCE: 19

Ser Asn Gly Gln Ala Thr His Asp Asn Gly Ala Gly Lys Pro Val
1               5                   10                  15

<210> SEQ ID NO 20
<211> LENGTH: 15
<212> TYPE: PRT
<213> ORGANISM: artificial
<220> FEATURE:
<223> OTHER INFORMATION: variant of JCV peptide

<400> SEQUENCE: 20

Ser Asn Gly Gln Ala Ala His Asp Asn Gly Ala Gly Lys Pro Val
1               5                   10                  15
```

```
<210> SEQ ID NO 21
<211> LENGTH: 15
<212> TYPE: PRT
<213> ORGANISM: artificial
<220> FEATURE:
<223> OTHER INFORMATION: variant of JCV peptide

<400> SEQUENCE: 21

Ser Asn Gly Gln Ala Ser His Asp Asn Gly Ala Gly Lys Pro Val
1               5                   10                  15

<210> SEQ ID NO 22
<211> LENGTH: 15
<212> TYPE: PRT
<213> ORGANISM: JC virus

<400> SEQUENCE: 22

Ala Gly Lys Pro Val Gln Gly Thr Ser Phe His Phe Phe Ser Val
1               5                   10                  15

<210> SEQ ID NO 23
<211> LENGTH: 15
<212> TYPE: PRT
<213> ORGANISM: JC virus

<400> SEQUENCE: 23

His Phe Phe Ser Val Gly Gly Glu Ala Leu Glu Leu Gln Gly Val
1               5                   10                  15

<210> SEQ ID NO 24
<211> LENGTH: 15
<212> TYPE: PRT
<213> ORGANISM: artificial
<220> FEATURE:
<223> OTHER INFORMATION: variant of JCV peptide

<400> SEQUENCE: 24

Ala Leu Glu Leu Gln Gly Val Leu Phe Asn Tyr Arg Thr Lys Tyr
1               5                   10                  15

<210> SEQ ID NO 25
<211> LENGTH: 15
<212> TYPE: PRT
<213> ORGANISM: artificial
<220> FEATURE:
<223> OTHER INFORMATION: variant of JCV peptide

<400> SEQUENCE: 25

Ala Leu Glu Leu Gln Gly Val Leu Phe Asn Tyr Arg Thr Thr Tyr
1               5                   10                  15

<210> SEQ ID NO 26
<211> LENGTH: 15
<212> TYPE: PRT
<213> ORGANISM: artificial
<220> FEATURE:
<223> OTHER INFORMATION: variant of JCV peptide

<400> SEQUENCE: 26

Tyr Arg Thr Lys Tyr Pro Asp Gly Thr Ile Phe Pro Lys Asn Ala
1               5                   10                  15

<210> SEQ ID NO 27
<211> LENGTH: 15
<212> TYPE: PRT
<213> ORGANISM: artificial
<220> FEATURE:
```

```
<223> OTHER INFORMATION: variant of JCV peptide

<400> SEQUENCE: 27

Tyr Arg Thr Thr Tyr Pro Asp Gly Thr Ile Phe Pro Lys Asn Ala
1               5                   10                  15

<210> SEQ ID NO 28
<211> LENGTH: 15
<212> TYPE: PRT
<213> ORGANISM: artificial
<220> FEATURE:
<223> OTHER INFORMATION: variant of JCV peptide

<400> SEQUENCE: 28

Tyr Arg Thr Thr Tyr Pro His Gly Thr Ile Phe Pro Lys Asn Ala
1               5                   10                  15

<210> SEQ ID NO 29
<211> LENGTH: 16
<212> TYPE: PRT
<213> ORGANISM: JC virus

<400> SEQUENCE: 29

Phe Pro Lys Asn Ala Thr Val Gln Ser Gln Val Met Asn Thr Glu His
1               5                   10                  15

<210> SEQ ID NO 30
<211> LENGTH: 15
<212> TYPE: PRT
<213> ORGANISM: JC virus

<400> SEQUENCE: 30

Met Asn Thr Glu His Lys Ala Tyr Leu Asp Lys Asn Lys Ala Tyr
1               5                   10                  15

<210> SEQ ID NO 31
<211> LENGTH: 16
<212> TYPE: PRT
<213> ORGANISM: JC virus

<400> SEQUENCE: 31

Lys Asn Lys Ala Tyr Pro Val Glu Cys Trp Val Pro Asp Pro Thr Arg
1               5                   10                  15

<210> SEQ ID NO 32
<211> LENGTH: 15
<212> TYPE: PRT
<213> ORGANISM: JC virus

<400> SEQUENCE: 32

Pro Asp Pro Thr Arg Asn Glu Asn Thr Arg Tyr Phe Gly Thr Leu
1               5                   10                  15

<210> SEQ ID NO 33
<211> LENGTH: 15
<212> TYPE: PRT
<213> ORGANISM: JC virus

<400> SEQUENCE: 33

Asn Thr Arg Tyr Phe Gly Thr Leu Thr Gly Gly Glu Asn Val Pro
1               5                   10                  15

<210> SEQ ID NO 34
<211> LENGTH: 15
<212> TYPE: PRT
```

<213> ORGANISM: artificial
<220> FEATURE:
<223> OTHER INFORMATION: variant of JCV peptide

<400> SEQUENCE: 34

Gly Glu Asn Val Pro Pro Val Leu His Ile Thr Asn Thr Ala Thr
1 5 10 15

<210> SEQ ID NO 35
<211> LENGTH: 15
<212> TYPE: PRT
<213> ORGANISM: artificial
<220> FEATURE:
<223> OTHER INFORMATION: variant of JCV peptide

<400> SEQUENCE: 35

Gly Glu Asn Val Pro Ser Val Leu His Ile Thr Asn Thr Ala Thr
1 5 10 15

<210> SEQ ID NO 36
<211> LENGTH: 15
<212> TYPE: PRT
<213> ORGANISM: artificial
<220> FEATURE:
<223> OTHER INFORMATION: variant of JCV peptide

<400> SEQUENCE: 36

Gly Glu Asn Val Pro Pro Val Leu His Ile Thr Lys Thr Ala Thr
1 5 10 15

<210> SEQ ID NO 37
<211> LENGTH: 15
<212> TYPE: PRT
<213> ORGANISM: artificial
<220> FEATURE:
<223> OTHER INFORMATION: variant of JCV peptide

<400> SEQUENCE: 37

Ile Thr Asn Thr Ala Thr Thr Val Leu Leu Asp Glu Phe Gly Val
1 5 10 15

<210> SEQ ID NO 38
<211> LENGTH: 15
<212> TYPE: PRT
<213> ORGANISM: artificial
<220> FEATURE:
<223> OTHER INFORMATION: variant of JCV peptide

<400> SEQUENCE: 38

Ile Thr Lys Thr Ala Thr Thr Val Leu Leu Asp Glu Phe Gly Val
1 5 10 15

<210> SEQ ID NO 39
<211> LENGTH: 15
<212> TYPE: PRT
<213> ORGANISM: artificial
<220> FEATURE:
<223> OTHER INFORMATION: variant of JCV peptide

<400> SEQUENCE: 39

Asp Glu Phe Gly Val Gly Pro Leu Cys Lys Gly Asp Asn Leu Tyr
1 5 10 15

<210> SEQ ID NO 40
<211> LENGTH: 15
<212> TYPE: PRT
<213> ORGANISM: artificial

```
<220> FEATURE:
<223> OTHER INFORMATION: variant of JCV peptide

<400> SEQUENCE: 40

Asp Glu Phe Gly Val Arg Pro Leu Cys Lys Gly Asp Asn Leu Tyr
1               5                   10                  15

<210> SEQ ID NO 41
<211> LENGTH: 15
<212> TYPE: PRT
<213> ORGANISM: JC virus

<400> SEQUENCE: 41

Gly Asp Asn Leu Tyr Leu Ser Ala Val Asp Val Cys Gly Met Phe
1               5                   10                  15

<210> SEQ ID NO 42
<211> LENGTH: 15
<212> TYPE: PRT
<213> ORGANISM: artificial
<220> FEATURE:
<223> OTHER INFORMATION: variant of JCV peptide

<400> SEQUENCE: 42

Val Cys Gly Met Phe Thr Asn Arg Ser Gly Ser Gln Gln Trp Arg
1               5                   10                  15

<210> SEQ ID NO 43
<211> LENGTH: 15
<212> TYPE: PRT
<213> ORGANISM: JC virus

<400> SEQUENCE: 43

Arg Val Asp Asp Gly Gln Pro Met Tyr Gly Met Asp Ala Gln Val
1               5                   10                  15

<210> SEQ ID NO 44
<211> LENGTH: 14
<212> TYPE: PRT
<213> ORGANISM: JC virus

<400> SEQUENCE: 44

Met Ala Gln Val Glu Glu Val Arg Val Phe Glu Gly Thr Glu
1               5                   10

<210> SEQ ID NO 45
<211> LENGTH: 15
<212> TYPE: PRT
<213> ORGANISM: JC virus

<400> SEQUENCE: 45

Gly Asp Pro Asp Met Met Arg Tyr Val Asp Lys Tyr Gly Gln Leu
1               5                   10                  15

<210> SEQ ID NO 46
<211> LENGTH: 15
<212> TYPE: PRT
<213> ORGANISM: JC virus

<400> SEQUENCE: 46

Met Gly Ala Ala Leu Ala Leu Leu Gly Asp Leu Val Ala Thr Val
1               5                   10                  15

<210> SEQ ID NO 47
<211> LENGTH: 14
```

-continued

```
<212> TYPE: PRT
<213> ORGANISM: JC virus

<400> SEQUENCE: 47

Leu Val Ala Thr Val Ser Glu Ala Ala Ala Thr Gly Phe
1               5                   10

<210> SEQ ID NO 48
<211> LENGTH: 15
<212> TYPE: PRT
<213> ORGANISM: JC virus

<400> SEQUENCE: 48

Ala Ala Thr Gly Phe Ser Val Ala Glu Ile Ala Ala Gly Glu Ala
1               5                   10                  15

<210> SEQ ID NO 49
<211> LENGTH: 13
<212> TYPE: PRT
<213> ORGANISM: JC virus

<400> SEQUENCE: 49

Ala Ala Gly Glu Ala Ala Ala Thr Ile Val Glu Ile Ala
1               5                   10

<210> SEQ ID NO 50
<211> LENGTH: 13
<212> TYPE: PRT
<213> ORGANISM: JC virus

<400> SEQUENCE: 50

Glu Val Glu Ile Ala Ser Leu Ala Thr Val Glu Gly Ile
1               5                   10

<210> SEQ ID NO 51
<211> LENGTH: 15
<212> TYPE: PRT
<213> ORGANISM: JC virus

<400> SEQUENCE: 51

Thr Val Glu Gly Ile Thr Ser Thr Ser Glu Ala Ile Ala Ala Ile
1               5                   10                  15

<210> SEQ ID NO 52
<211> LENGTH: 15
<212> TYPE: PRT
<213> ORGANISM: JC virus

<400> SEQUENCE: 52

Ala Ile Ala Ala Ile Gly Leu Thr Pro Glu Thr Tyr Ala Val Ile
1               5                   10                  15

<210> SEQ ID NO 53
<211> LENGTH: 15
<212> TYPE: PRT
<213> ORGANISM: JC virus

<400> SEQUENCE: 53

Thr Tyr Ala Val Ile Thr Gly Ala Pro Gly Ala Val Ala Gly Phe
1               5                   10                  15

<210> SEQ ID NO 54
<211> LENGTH: 12
<212> TYPE: PRT
<213> ORGANISM: JC virus
```

-continued

```
<400> SEQUENCE: 54

Ala Val Ala Gly Phe Ala Ala Leu Val Gln Thr Val
1               5                   10

<210> SEQ ID NO 55
<211> LENGTH: 14
<212> TYPE: PRT
<213> ORGANISM: JC virus

<400> SEQUENCE: 55

Leu Val Gln Thr Val Thr Gly Gly Ser Ala Ile Ala Gln Leu
1               5                   10

<210> SEQ ID NO 56
<211> LENGTH: 15
<212> TYPE: PRT
<213> ORGANISM: JC virus

<400> SEQUENCE: 56

Phe Ala Asp Ser Lys Asn Gln Lys Ser Ile Cys Gln Gln Ala Val
1               5                   10                  15

<210> SEQ ID NO 57
<211> LENGTH: 14
<212> TYPE: PRT
<213> ORGANISM: JC virus

<400> SEQUENCE: 57

Cys Gln Gln Ala Val Asp Thr Val Ala Ala Lys Gln Arg Val
1               5                   10

<210> SEQ ID NO 58
<211> LENGTH: 15
<212> TYPE: PRT
<213> ORGANISM: JC virus

<400> SEQUENCE: 58

Ala Lys Gln Arg Val Asp Ser Ile His Met Thr Arg Glu Glu Met
1               5                   10                  15

<210> SEQ ID NO 59
<211> LENGTH: 14
<212> TYPE: PRT
<213> ORGANISM: JC virus

<400> SEQUENCE: 59

Thr Arg Glu Glu Met Leu Val Glu Arg Phe Asn Phe Leu Leu
1               5                   10

<210> SEQ ID NO 60
<211> LENGTH: 15
<212> TYPE: PRT
<213> ORGANISM: JC virus

<400> SEQUENCE: 60

Ile Phe Gly Ala His Gly Asn Ala Val Leu Glu Gln Tyr Met Ala
1               5                   10                  15

<210> SEQ ID NO 61
<211> LENGTH: 14
<212> TYPE: PRT
<213> ORGANISM: JC virus

<400> SEQUENCE: 61
```

```
Glu Gln Tyr Met Ala Gly Val Ala Trp Ile His Cys Leu Leu
1               5                   10
```

<210> SEQ ID NO 62
<211> LENGTH: 15
<212> TYPE: PRT
<213> ORGANISM: JC virus

<400> SEQUENCE: 62

```
Val Ile Tyr Asp Phe Leu Lys Cys Ile Val Leu Asn Ile Pro Lys
1               5                   10                  15
```

<210> SEQ ID NO 63
<211> LENGTH: 15
<212> TYPE: PRT
<213> ORGANISM: JC virus

<400> SEQUENCE: 63

```
Leu Asn Ile Pro Lys Lys Arg Tyr Trp Leu Phe Lys Gly Pro Ile
1               5                   10                  15
```

<210> SEQ ID NO 64
<211> LENGTH: 15
<212> TYPE: PRT
<213> ORGANISM: JC virus

<400> SEQUENCE: 64

```
Val Phe Glu Asp Val Lys Gly Thr Gly Ala Glu Ser Arg Asp Leu
1               5                   10                  15
```

<210> SEQ ID NO 65
<211> LENGTH: 14
<212> TYPE: PRT
<213> ORGANISM: JC virus

<400> SEQUENCE: 65

```
Glu Ser Arg Asp Leu Pro Ser Gly His Gly Ile Ser Asn Leu
1               5                   10
```

<210> SEQ ID NO 66
<211> LENGTH: 16
<212> TYPE: PRT
<213> ORGANISM: JC virus

<400> SEQUENCE: 66

```
Gly Ile Ser Asn Leu Asp Cys Leu Arg Asp Tyr Leu Asp Gly Ser Val
1               5                   10                  15
```

<210> SEQ ID NO 67
<211> LENGTH: 15
<212> TYPE: PRT
<213> ORGANISM: JC virus

<400> SEQUENCE: 67

```
Asp Tyr Leu Asp Gly Ser Val Lys Val Asn Leu Glu Arg Lys His
1               5                   10                  15
```

<210> SEQ ID NO 68
<211> LENGTH: 15
<212> TYPE: PRT
<213> ORGANISM: JC virus

<400> SEQUENCE: 68

```
Val Asn Leu Glu Arg Lys His Gln Asn Lys Arg Thr Gln Val Phe
```

<210> SEQ ID NO 69
<211> LENGTH: 14
<212> TYPE: PRT
<213> ORGANISM: JC virus

<400> SEQUENCE: 69

Cys Thr Phe His Ile Cys Lys Gly Phe Gln Cys Phe Lys Lys
1               5                   10

<210> SEQ ID NO 70
<211> LENGTH: 15
<212> TYPE: PRT
<213> ORGANISM: artificial
<220> FEATURE:
<223> OTHER INFORMATION: variant of JCV peptide

<400> SEQUENCE: 70

Val Gly Cys Asp Phe Pro Pro Asn Ser Asp Thr Leu Tyr Cys Lys
1               5                   10                  15

<210> SEQ ID NO 71
<211> LENGTH: 15
<212> TYPE: PRT
<213> ORGANISM: artificial
<220> FEATURE:
<223> OTHER INFORMATION: variant of JCV peptide

<400> SEQUENCE: 71

Val Ser Cys Asp Phe Pro Pro Asn Ser Asp Thr Leu Tyr Cys Lys
1               5                   10                  15

<210> SEQ ID NO 72
<211> LENGTH: 15
<212> TYPE: PRT
<213> ORGANISM: JC virus

<400> SEQUENCE: 72

Arg Lys Phe Leu Arg Ser Ser Pro Leu Val Trp Ile Asp Cys Tyr
1               5                   10                  15

<210> SEQ ID NO 73
<211> LENGTH: 14
<212> TYPE: PRT
<213> ORGANISM: JC virus

<400> SEQUENCE: 73

Trp Ile Asp Cys Tyr Cys Phe Asp Cys Phe Arg Gln Trp Phe
1               5                   10

<210> SEQ ID NO 74
<211> LENGTH: 15
<212> TYPE: PRT
<213> ORGANISM: JC virus

<400> SEQUENCE: 74

Phe Arg Gln Trp Phe Gly Cys Asp Leu Thr Gln Glu Ala Leu His
1               5                   10                  15

<210> SEQ ID NO 75
<211> LENGTH: 14
<212> TYPE: PRT
<213> ORGANISM: JC virus

<400> SEQUENCE: 75

```
Asp Leu Thr Gln Glu Ala Leu His Cys Trp Glu Lys Val Leu
1               5                   10
```

<210> SEQ ID NO 76
<211> LENGTH: 15
<212> TYPE: PRT
<213> ORGANISM: JC virus

<400> SEQUENCE: 76

```
Trp Glu Lys Val Leu Gly Asp Thr Pro Tyr Arg Asp Leu Lys Leu
1               5                   10                  15
```

<210> SEQ ID NO 77
<211> LENGTH: 15
<212> TYPE: PRT
<213> ORGANISM: artificial
<220> FEATURE:
<223> OTHER INFORMATION: variant of JCV peptide

<400> SEQUENCE: 77

```
His Phe Arg Gly Phe Ser Lys Ser Ile Ser Ile Ser Asp Thr Phe
1               5                   10                  15
```

<210> SEQ ID NO 78
<211> LENGTH: 15
<212> TYPE: PRT
<213> ORGANISM: artificial
<220> FEATURE:
<223> OTHER INFORMATION: variant of JCV peptide

<400> SEQUENCE: 78

```
Val Cys Gly Met Phe Thr Asn Arg Ser Gly Tyr Gln Gln Trp Arg
1               5                   10                  15
```

<210> SEQ ID NO 79
<211> LENGTH: 15
<212> TYPE: PRT
<213> ORGANISM: artificial
<220> FEATURE:
<223> OTHER INFORMATION: variant of JCV peptide

<400> SEQUENCE: 79

```
His Leu Arg Gly Phe Ser Asn Ser Ile Ser Ile Ser Asp Thr Phe
1               5                   10                  15
```

<210> SEQ ID NO 80
<211> LENGTH: 15
<212> TYPE: PRT
<213> ORGANISM: artificial
<220> FEATURE:
<223> OTHER INFORMATION: variant of JCV peptide

<400> SEQUENCE: 80

```
His Leu Arg Gly Phe Ser Lys Ser Ile Ser Ile Ser His Thr Phe
1               5                   10                  15
```

<210> SEQ ID NO 81
<211> LENGTH: 15
<212> TYPE: PRT
<213> ORGANISM: artificial
<220> FEATURE:
<223> OTHER INFORMATION: variant of JCV peptide

<400> SEQUENCE: 81

```
Ile Ser His Thr Phe Glu Ser Asp Ser Pro Asn Arg Asp Met Leu
1               5                   10                  15
```

<210> SEQ ID NO 82
<211> LENGTH: 15
<212> TYPE: PRT
<213> ORGANISM: artificial
<220> FEATURE:
<223> OTHER INFORMATION: variant of JCV peptide

<400> SEQUENCE: 82

Gly Glu Asn Ile Pro Pro Val Leu His Ile Thr Asn Thr Ala Thr
1               5                   10                  15

<210> SEQ ID NO 83
<211> LENGTH: 15
<212> TYPE: PRT
<213> ORGANISM: artificial
<220> FEATURE:
<223> OTHER INFORMATION: variant of JCV peptide

<400> SEQUENCE: 83

Val Cys Gly Met Phe Thr Asp Arg Ser Gly Ser Gln Gln Trp Arg
1               5                   10                  15

<210> SEQ ID NO 84
<211> LENGTH: 15
<212> TYPE: PRT
<213> ORGANISM: artificial
<220> FEATURE:
<223> OTHER INFORMATION: variant of JCV peptide

<400> SEQUENCE: 84

Val Cys Gly Met Phe Thr Asn Arg Phe Gly Ser Gln Gln Trp Arg
1               5                   10                  15

<210> SEQ ID NO 85
<211> LENGTH: 15
<212> TYPE: PRT
<213> ORGANISM: artificial
<220> FEATURE:
<223> OTHER INFORMATION: variant of JCV peptide

<400> SEQUENCE: 85

Val Cys Gly Met Phe Thr Asn Arg Ser Gly Ser Gln His Trp Arg
1               5                   10                  15

<210> SEQ ID NO 86
<211> LENGTH: 15
<212> TYPE: PRT
<213> ORGANISM: artificial
<220> FEATURE:
<223> OTHER INFORMATION: variant of JCV peptide

<400> SEQUENCE: 86

His Leu Arg Gly Phe Ser Lys Leu Ile Ser Ile Ser Asp Thr Phe
1               5                   10                  15

<210> SEQ ID NO 87
<211> LENGTH: 15
<212> TYPE: PRT
<213> ORGANISM: artificial
<220> FEATURE:
<223> OTHER INFORMATION: variant of JCV peptide

<400> SEQUENCE: 87

His Leu Arg Gly Phe Ser Glu Ser Ile Ser Ile Ser Asp Thr Phe
1               5                   10                  15

```
<210> SEQ ID NO 88
<211> LENGTH: 15
<212> TYPE: PRT
<213> ORGANISM: artificial
<220> FEATURE:
<223> OTHER INFORMATION: variant of JCV peptide

<400> SEQUENCE: 88

Val Cys Gly Met Phe Thr His Arg Ser Gly Ser Gln Gln Trp Arg
1               5                   10                  15

<210> SEQ ID NO 89
<211> LENGTH: 15
<212> TYPE: PRT
<213> ORGANISM: artificial
<220> FEATURE:
<223> OTHER INFORMATION: variant of JCV peptide

<400> SEQUENCE: 89

Val Cys Gly Met Phe Thr Thr Arg Ser Gly Ser Gln Gln Trp Arg
1               5                   10                  15

<210> SEQ ID NO 90
<211> LENGTH: 15
<212> TYPE: PRT
<213> ORGANISM: artificial
<220> FEATURE:
<223> OTHER INFORMATION: variant of JCV peptide

<400> SEQUENCE: 90

Val Cys Gly Met Phe Thr Asn Arg Tyr Gly Ser Gln Gln Trp Arg
1               5                   10                  15

<210> SEQ ID NO 91
<211> LENGTH: 15
<212> TYPE: PRT
<213> ORGANISM: artificial
<220> FEATURE:
<223> OTHER INFORMATION: variant of JCV peptide

<400> SEQUENCE: 91

Val Cys Gly Met Phe Thr Asn Arg Leu Gly Ser Gln Gln Trp Arg
1               5                   10                  15

<210> SEQ ID NO 92
<211> LENGTH: 15
<212> TYPE: PRT
<213> ORGANISM: artificial
<220> FEATURE:
<223> OTHER INFORMATION: variant of JCV peptide

<400> SEQUENCE: 92

Val Cys Gly Met Phe Thr Asn Arg Ser Gly Cys Gln Gln Trp Arg
1               5                   10                  15
```

POLYOMA VIRUS JC PEPTIDES AND PROTEINS IN VACCINATION AND DIAGNOSTIC APPLICATIONS

RELATED APPLICATIONS

This application is a 35 U.S.C. 371 national stage filing of International Application No. PCT/EP2012/064445, filed on Jul. 23, 2012, which claims priority to European Patent Application No. 11006031.6, filed on Jul. 22, 2011. The contents of the aforementioned applications are hereby incorporated by reference.

The present invention relates to the field of vaccination or immunization, in particular therapeutic vaccination, and diagnosis. Pharmaceutical compositions and kits capable of eliciting a protective immune response against polyoma virus JC (JCV) are disclosed, which may be used e.g., for therapy or for prevention of progressive multifocal leukoencephalopathy (PML) and/or progressive multifocal leukoencephalopathy-immune reconstitution inflammatory syndrome (PML-IRIS). Individuals in danger of such PML or PML-IRIS may, e.g., be immunocompromised or immunosuppressed patients or patients having an autoimmune disease eligible for immunosuppressive treatment. The invention also relates to compositions comprising at least one CD4+ epitope of a JCV protein and to therapeutic, prophylactic and diagnostic uses thereof.

Progressive multifocal leukoencephalopathy and progressive multifocal leukoencephalopathy-immune reconstitution inflammatory syndrome are caused by infection of the central nervous system with the polyoma virus JC (JCV). Both have recently emerged as complications of monoclonal antibody therapy in multiple sclerosis and other autoimmune diseases.

Progressive multifocal leukoencephalopathy (PML) was first described in 1958. In 1971 the polyoma virus JC (JCV) was identified as causative agent of PML. PML is an opportunistic and often fatal infection that occurs in states of immunocompromise such as HIV infection, cancer, organ transplantation, immunodeficiencies, or rarely during autoimmune diseases. In AIDS patients, PML was one of the most serious complications, although its incidence decreased after introduction of antiretroviral therapy (Cinque et al., 2001). Infection with JCV is highly prevalent in healthy adults, and 60% or more of the population carries a latent/persistent infection (Egli et al., 2009). In recent years PML has emerged as an increasingly common serious adverse event in monoclonal antibody therapy of autoimmune diseases, in particular of multiple sclerosis (MS) and treatment with natalizumab (anti-VLA-4) (Kleinschmidt-DeMasters and Tyler, 2005) (Langer-Gould et al., 2005) (Jilek et al.) (Anonymous, 2011). Other monoclonal antibodies such as rituximab (anti-CD20), infliximab (anti-tumor necrosis factor (TNF)-alpha) and the IgG1-TNF receptor 2 fusion protein etanercept that are used to treat rheumatoid arthritis (RA) have also been associated with PML. Efalizumab (anti-leukocyte function-associated antigen-1) had to be withdrawn from the market already (Pugashetti and Koo, 2009). With >120 PML cases reported in MS patients receiving natalizumab, the PML incidence is between 1:500 and 1:1.000 and jeopardizes the use of this highly effective treatment (Anonymous, 2011).

The pathogenesis of PML is characterized by a lytic infection of myelin-forming oligodendrocytes and abortive infection of astrocytes in the absence of a notable immune reaction. However, other CNS cells such as cerebellar granule neurons can also be infected by JCV (Du Pasquier et al., 2003a). Although the mechanisms of controlling JCV infection are as yet incompletely understood, latency of JCV infection is probably controlled by effective humoral and/or cellular immune responses in healthy individuals (Du Pasquier et al., 2001) (Du Pasquier et al., 2004a) (Weber et al., 1997). Accordingly, the presence of JCV-specific CD8+ cytotoxic T cells has been linked to the recovery from PML, while these cells were absent in PML cases with fatal outcome (Du Pasquier et al., 2004a; Du Pasquier et al., 2006; Koralnik et al., 2002). Also, PML occurs preferentially in situations of decreased CD4+ T cell numbers or compromised CD4+ cell functions such as AIDS and idiopathic CD4+ lymphopenia (Stoner et al., 1986) (Gillespie et al., 1991; Zonios et al., 2008). Comparable to the role of CD8+ JCV-specific T cells, the resolution of PML follows the restoration of CD4+ number and function, indicating that both CD4+ and CD8+ virus-specific T cells are crucial for host protection.

In contrast to the profound immunosuppression in AIDS, in Non-Hodgkin lymphoma and leukemias, monoclonal antibody-based therapies inhibit specific immune functions such as cell migration across endothelial barriers in anti-VLA-4/natalizumab therapy, or eliminate certain immune cells such as CD20-expressing B cells in the case of rituximab (Lutterotti and Martin, 2008). In the context of anti-VLA-4 therapy current hypotheses assume that PML results from compromised immune surveillance of the CNS, since activated T cells and CD209+ immature dendritic cells cannot cross the blood-brain-barrier (BBB) and access the brain (del Pilar Martin et al., 2008; Stuve et al., 2006; Yednock et al., 1992). As a result, local antigen presentation in the CNS is compromised (del Pilar Martin et al., 2008).

Alternatively, it has been considered that the inhibition of VLA-4/vascular cell adhesion molecule-1 (VCAM-1) interactions, which serve as a retention signal for hematopoietic precursor cells in the bone marrow, leads to release of JCV from one of its natural niches (Tan et al., 2009a), increased viral replication and occurrence of JCV variants with tropism for CNS cells (Houff et al., 1988; Ransohoff, 2005).

Cessation of therapy with these monoclonal antibodies in PML reestablishes immunological surveillance for JCV-infected cells in the CNS and leads to clinically apparent inflammatory responses in this compartment. Inflammation can be visualized by contrast-enhancing lesions on magnetic resonance imaging (MRI) due to opening of the BBB and influx of T cells and monocytes/macrophages. The latter manifestation of PML has been termed immune PML-reconstitution inflammatory syndrome (PML-IRIS) (Koralnik, 2006; Tan et al., 2009b). PML-IRIS can lead to rapid deterioration of the patient's clinical state and death in about 30% to 50% of cases (Tan et al., 2009b). Its cellular and molecular pathogenesis, i.e. which T cell subtypes, antibodies or cytokines are involved, is currently poorly understood.

Progressive multifocal leukoencephalopathy-immune reconstitution inflammatory syndrome may obscure the diagnosis of progressive multifocal leukoencephalopathy and lead to marked immunopathogenesis with severe clinical disability and possibly death. Different from progressive multifocal leukoencephalopathy, in which demyelination results from oligodendrocyte lysis by JC virus in the absence of an immune response at the site of infection, tissue destruction in progressive multifocal leukoencephalopathy-immune reconstitution inflammatory syndrome is caused by a vigorous immune response against JC virus-infected oligodendrocytes and astrocytes and inflammatory swelling of the brain. PML-IRIS starts when immunocompetence is reestablished, e.g. in AIDS patients treated with highly active retroviral therapy or in MS patients treated with the anti-VLA-4 monoclonal antibody natalizumab and after washing out the antibody. During PML-IRIS, immune cells enter the brain and eliminate JCV-infected astrocytes and oligodendrocytes. The cells and mediators that are involved in progressive multifocal leukoencephalopathy-immune reconstitution inflammatory syndrome are poorly understood in the state of the art.

Diagnosing PML and PML-IRIS as early as possible and identifying effective therapies based on the underlying disease mechanisms are important goals not only in MS, but also in a number of other autoimmune diseases, during acquired immunodeficiencies, during malignancies and in transplant medicine. Methods for diagnosis of JCV are known. For example, it is possible to detect the virus by PCR. An alternative approach is detection of antibodies to JCV, e.g., by ELISA. Exemplary methods for diagnosing JCV infection, e.g., using an ELISA to the JCV core protein VP1 are taught in Goldmann et al., 1999, or in DE 195 43 553.

Methods of treatment of the disease have been researched less so far. Goldmann et al., 1999, or DE 195 43 553 suggest vaccination with VP1 protein, which may be assembled to virus like particles. It is taught that vaccination with Freund's Complete Adjuvant (FCA) induces an immune response, while vaccination without adjuvant is not immunogenic. However, Freund's Complete Adjuvant may not be used in humans due to its toxicity.

In light of the dangers of a pathogenic immune response, as prevalent in PML-IRIS, it is a particular challenge to develop a vaccination which allows for treatment of PML and prevention of PML and PML-IRIS.

This problem was solved by the invention, in particular, by the subject matter of the claims.

The present invention provides in a first aspect a protein or peptide comprising at least one CD4+ epitope derived from JCV, wherein the epitope is selected from the group comprising SEQ ID NO: 1-92. In a second aspect, the invention provides a pharmaceutical kit comprising a protein or peptide comprising at least one CD4+ epitope derived from JCV, wherein the epitope is selected from the group comprising SEQ ID NO: 1-92, and an adjuvant. Preferably, the adjuvant is selected from the group comprising a TLR-7 agonist and/or TLR-8 agonist.

The inventors have surprisingly shown the biological relevance of the CD4+ response in controlling JCV infection and preventing PML. It was previously believed that the main role in controlling JCV was played by CD8+ cells and the cellular immune response.

The inventors identified a number of CD4+ epitopes, in particular from the VP1 protein of JCV which are suitable for being used in therapeutic and prophylactic vaccines. For example, the peptides or proteins for use in these vaccines can comprise one or more of the epitope sequence from one or more of the JCV proteins disclosed herein. The protein or peptide of the invention can, for example, comprise the amino acid sequence of the VP 1 protein or a protein having at least 70% amino acid identity with the VP1 protein. According to a preferred aspect, the invention refers to vaccination with the VP1 protein or a protein having at least 70% amino acid identity with VP1. The VP1 protein or its variant can be present in the vaccine as a pentamer, i.e. in the form of a JCV capsomer. Preferably, however, the VP1 protein or its variant is present in the form of a virus-like particle (VLP). The VLP can consist of VP1 or it may also comprise other JCV proteins, such VP2 and/or VP3. The pharmaceutical kit of the invention may thus comprise, as one component, an antigen, i.e., a protein or peptide comprising at least one CD4+ epitope derived from JCV comprises VP1 or a protein having at least 70% amino acid identity with VP1.

Protein and peptide are used largely in exchange for each other in the context of this application. Typically, proteins are longer than peptides, and, e.g., comprise more than 100 amino acids, while peptides have between 5 and 100 amino acids.

A CD4+ epitope is a peptide capable of being recognized by a CD4+ T cell's T cell receptor in the context of a MHC class II molecule. The inventors have identified CD4+ T cell epitopes, which are recognized by CD4+ T cells of healthy controls and patients having PML/PML-IRIS. These peptides are disclosed in Table 1 below (SEQ ID NO: 1-92). Several of these epitopes could not be identified by classical methods using peripheral T cells, but were only identified as reactive with T cells isolated from the brain biopsy of a patient with PML-IRIS. Since this patient showed low to absent JCV viral load in the brain and CSF, the JCV-specific intracerebral CD4+-mediated immune response appears to have cleared or almost cleared the viral infection from the brain, and therefore the experiments performed ensure the high biological relevance of the identified CD4+ T cell epitopes, in particular those identified as recognized by brain-derived T cells. T cell epitopes that have been identified by brain-derived T cells are depicted in SEQ ID NO:1-3, 7-9, 11, 23, 37-38, 43-45, and 69-71 and peptides and proteins comprising these epitopes are particularly preferred for the prophylactic and therapeutic vaccination approaches described herein. In a preferred embodiment, the protein or peptide of the invention comprises at least one CD4+ epitope selected from the group comprising SEQ ID NO:1-3, 7-9, 11, 23, 37-38, 43-45, and 69-71.

VP1 is the major capsid protein of JCV, and comprises a high proportion of the identified immunodominant epitopes. The sequence of wild type VP1 is disclosed, e.g., in DE 195 43 553. VP1 can, however, also be mutated, e.g., in positions 55, 269 and others. It has been shown that more than 50% of the VP1 mutations occurring in vivo are in those positions. Epitopes corresponding to peptides from mutated VP1 proteins may also be employed in the context of the invention. Some of the peptides in Table 1 correspond to mutated VP1 fragments. The proteins or peptides comprising a CD4+ epitope of the invention consist of the peptides of SEQ ID NO:1-92, or they may be longer, e.g., having a length of 12, 13, 14, 15, 16, 17, 18, 19, 20, 21, 21, 22, 23, 24, 25, 26, 27, 28, 29, 30, 31, 32, 33, 34, 35, or more, 40 or more, 50 or more, 75 or more, 100 or more, 125 or more, 150 or more or 200 or more amino acids. They may consist of amino acids of wild type or naturally occurring mutated VP1 or other JCV proteins or comprise different sequences, such as sequences not originating from the same virus protein or not in their natural arrangement. E.g., they may be fusion proteins comprising 2, 3, 4, 5, 6, 7, 8, 9, 10 or more epitopes selected from the group comprising SEQ ID NO: 1-92.

In one embodiment, the protein has at least 70% amino acid identity with VP1. Preferably, it comprises at least one epitope selected from the group comprising SEQ ID NO: 1-92. The protein having at least 70% amino acid identity with VP1 may be a fusion protein further comprising at least one epitope selected from the group comprising SEQ ID NO: 1 and SEQ ID NO: 46-76. Preferably, the protein comprises at least one of the epitopes depicted in SEQ ID NO:1-3, 7-9, 11, 23, 37-38, 43-45, and 69-71

In one embodiment, the protein comprising at least one CD4+ epitope derived from JCV is present in the form of a virus like particle. VP1 protein or derivatives thereof, e.g., mutants or fragments comprising at least 70% amino acid sequence identity to wild type VP1 as described in DE 195 43 553, or fusion proteins thereof, can assemble into virus like particles, which is also described in DE 195 43 553.

Of course, the kit of the invention may also comprise two or more peptides or proteins comprising at least one CD4+ epitope derived from JCV selected from the group of SEQ ID NO:1-92, preferably, in one composition. Preferably, the kit comprises two or more peptides or proteins having CD4+ epitopes from JCV selected from the group of SEQ ID NO: 1-3, 7-9, 11, 23, 37-38, 43-45, and 69-71. As both CD4+ epitopes and CD8+ epitopes appear to be relevant for an effective immune response against JCV, it is particularly advantageous if the peptide or protein of the invention comprises both at least one CD4+ epitope and one CD8+ epitope.

As demonstrated in the Examples of the present invention, the peptides and proteins of the invention are useful for being administered to a subject who is afflicted with PML to induce or enhance a specific intracerebral CD4+-mediated immune response against JCV. Thus, according to one aspect of the invention, the protein or peptide comprising the at least one CD4+ epitope derived from JCV is used in a method of treating PML in a subject. The treatment of a subject who already suffers from PML and/or PML-IRIS is referred to herein as therapeutic vaccination. In a preferred embodiment, a protein comprising the amino acid sequence of the VP1 protein or the amino acid sequence of a protein having at least 70% amino acid identity with VP1 is used in the treatment of PML. In another preferred embodiment, the peptide or protein used in the treatment of PML comprises or consists of an epitope selected from the group of SEQ ID NO:1-3, 7-9, 11, 23, 37-38, 43-45, and 69-71.

When treating subjects who developed a PML, it has been found that treatment based on the administration of the peptides or proteins of the invention can be further improved by administration of a cytokine capable of expanding and maintaining T cells. It has been found in the course of the invention that the co-administration of such a cytokine provides a stimulus for reconstitution of important immune functions. Several cytokines can be used, e.g., IL-7, IL-2, IL-15 and IL-21. The use of IL-7 or derivatives of IL-7 is particularly preferred.

In a still further embodiment, PML treatment by therapeutic vaccination also comprises the administration of an adjuvant. The adjuvant can be any adjuvant which is suitable for being administered to a human subject and results in T cell activation and/or antigen presentation at the site of administration. For example, the adjuvant to be used in the methods and kits of the present invention may be selected from the group of MF59, aluminium hydroxide, calcium phosphate gel, lipopolysaccharides, imidazo-quinolines (e.g. imiquimod, S-28463), oligonucleotide sequences with CpG motifs, stearyl tyrosine, DTP-GDP, DTP-DPP, threonyl-MDP, 7-allyl-8-oxoguanosine, glycolipid bay R1005, multi-antigen peptide system, polymerized haptenic peptides, bacterial extracts, TLR-7 agonists, TLR-8 agonists, vit-A, and the like.

Preferably, the adjuvant f to be used in practising the invention is a TLR-7 agonist or a TLR-8 agonist. Several TLR-7 agonists are known and commercially available, e.g., from Invivogen, San Diego. Examples are the adenine analog CL264, the guanosine analogue Loxoribine, or, preferably, imidazoquinoline compounds such as Resiquimod, Gardiquimod™ or Imiquimod (4-amino-1-isobutyl-1H-imidazol[4,5-c]chinolin). TLR-8 agonists are known to have similar biological effects as TLR-7 agonists and can thus also, or alternatively, be used. Examples of TLR-8 agonists are singlestranded RNAs or E. coli RNA. Exemplary TLR-7/8 Ligands are the thiazoloquinoline compound CL075, the imidazoquinoline compound R848, or the water-soluble R848 imidazoquinoline compound CL097, thymidine homopolymer phosphorothioate ODN (Poly(dT).

The preferred adjuvant used in the invention is imiquimod. More than one adjuvant, preferably selected from the group comprising a TLR-7 agonist and/or TLR-8 agonist, can be used in the context of the invention, and if required, additional means to stimulate an immune response can be employed, e.g., as described below.

According to a preferred embodiment, therapeutic vaccination comprises the administration of VP1 (or a protein having at least 70% amino acid identity with VP1) in combination with an adjuvant, such as imiquimod, and a cytokine, such as IL-7. The VP1 protein or its variant can be present in this combination as a pentamer, i.e. in the form of a JCV capsomer. Preferably, however, the VP1 protein or its variant is present in the form of a virus-like particle (VLP). The VLP can consist of VP1 or it may also comprise other JCV proteins, such VP2 and/or VP3. It is particularly preferred that a VLP consisting of VP1 or a protein having at least 70% amino acid identity with VP1 is administered in combination with an adjuvant and a cytokine. Most preferably, the VLP consisting of VP1 is administered in combination with imiquimod and IL-7 for therapeutic vaccination.

In one embodiment, e.g., the kit may further comprise IL-7. IL-7 is preferably used in cases where a subject suffering from PML is treated (i.e. in a therapeutic vaccination) and no sufficient immune response is expected without further stimulation, e.g., if the patient is immunodeficient. It was shown by the inventors that administration of IL-7 with the other components of the kit was able to induce a protective immune response in an individual with a congenital immune defect. IL-7 may also be employed in subjects receiving immunosuppressive medication or in patients immunocompromised due to HIV infection.

Preferably, the protein or peptide of the invention comprising at least one CD4+ epitope derived from JCV is to be administered subcutaneously. Other modes of administration may also be chosen, e.g., dermal, intramuscular, intravenous, pulmonary or oral administration.

The adjuvant is preferably to be administered to the subject in a way suitable for inducing an immune response to the protein or peptide of the invention. For example, the adjuvant may be administered in the same way and at the time of administration of the protein or peptide of the invention, and both may be in one composition, e.g., contained in one vial. In one embodiment, both the protein or peptide comprising the CD4+ epitope and the adjuvant are for subcutaneous administration. Alternatively, they are administered in a way which allows stimulation of an immune response to the epitope, e.g., the antigen is administered subcutaneously and the adjuvant is administered topically or dermally, in particular, it may be administered at the site of the injection of the antigen, e.g., in a form or a cream or lotion. Ways of dermal application of adjuvants such as imiquimod are known in the state of the art. For example, a cream comprising an effective concentration of the adjuvant may be administered to the skin in the vicinity of the subcutaneous injection over an area of about 5 cm×5 cm.

The adjuvant and the antigen are preferably to be administered simultaneously, or consecutively within a short time span. For example, an imiquimod cream may be dermally administered directly after subcutaneous injection. The cream may be covered to prevent further spreading, and wiped off after about 4-12 hours, e.g., 8 hours.

After the first administration of the protein or peptide comprising at least one of the CD4+ epitopes and the adjuvant, further courses of administration may be carried out for boosting the immune response, e.g., two, three or four courses of administration. The time between courses may be about 1 to about 4 weeks, preferably, about 2 to about 3 weeks, e.g., 10 days. In one embodiment, the first administration is followed by a booster immunisation after 2 weeks and another after 6 weeks. In an immunodeficient or immunocompromised subject, it is advantageous to administrate both antigen and adjuvant for boosting. In a subject who is not immunodeficient or immunocompromised, it is also possible to only use adjuvant for the first, or for the first and second immunisation, i.e. to use the antigen only for later immunisations.

Apart from being used in the treatment of subjects which have developed PML, the protein or peptide of the invention can also effectively be used for preventing PML and/or PML-IRIS in a subject who has not yet developed PML, but is at risk of developing this disease. This approach is referred to herein as prophylactic vaccination. The subject to be treated by prophylactic vaccination can be a subject who is not yet infected with JCV, which means that prophylactic vaccination is used to prevent infection of the subject. Preferably, however, the subject to be treated by prophylactic vaccination is a subject who is already infected with JCV. Prophylactic vaccination does not need to include the administration of an adjuvant. It is preferred that prophylactic vaccination neither includes the administration of an adjuvant nor the administration of a cytokine such as IL-7. Prophylactic vaccination approaches can, however, also include the administration of these compounds to the respective subject.

According to a preferred aspect, prophylactic vaccination includes the administration of the VP1 protein or a protein having at least 70% amino acid identity with VP1. The VP1 protein or its variant can be present in the prophylactic vaccine as a pentamer, i.e. in the form of a JCV capsomer. Preferably, however, the VP1 protein or its variant is present in the prophylactic vaccine in the form of a virus-like particle (VLP). The VLP can consist of VP1 or it may also comprise other JCV proteins, such VP2 and/or VP3.

The subject to whom the protein or peptide of the invention is administered, either in a therapeutic or prophylactic vaccination regimen, has an inherited or acquired immunodeficiency, which means that several aspects of adaptive or innate immune function are dysfunctional or impaired. Said immunodeficiency may result from an inherited dysfunction such as idiopathic CD4+ lymphopenia or Hyper-IgE-Syndrome, or due to an acquired immunodeficiency resulting from a disease or pathological condition, such as AIDS, leukemia, lymphoma, multiple myeloma or infection with hepatitis virus B or C. The subject may also be immunocompromised as a result from a therapeutic intervention. For example, cancer treatment often involves chemotherapeutic or radiation courses that lead to certain dysfunctions of the immune system. Also, immunosuppressive treatments which are commonly used in transplantation medicine and also in the treatment of autoimmune diseases may be responsible for the immunodeficiency of the subject to be treated according to the invention.

According to a preferred embodiment, the subject to be treated by the peptides or proteins of the invention, either by prophylactic or therapeutic treatment, is undergoing an immunosuppressive treatment or will undergo an immunosuppressive treatment. This means that once it has been decided by the attending physician that a patient is to be treated by the administration of an immunosuppressive agent, it will be possible to administer to said patient one or more of the peptides or proteins of the present invention in order to prevent the development of PML and/or PML/IRIS. This is particularly useful, e.g., for patients which will receive organ transplantation.

Alternatively, the subject undergoing or being eligible for immunosuppressive treatment can be patients who suffer from an autoimmune disease, preferably an autoimmune disease which is characterized in that T cells play a pathogenetic role or are the target of immunosuppression. As used herein, autoimmune diseases comprise, for example, acute disseminated encephalomyelitis (ADEM), ankylosing spondylitis, antiphospholipid syndrome, autoimmune cardiomyopathy, autoimmune cardiomyopathy, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Behcet's disease, celiac disease, Crohn's disease, dermatomyositis, diabetes mellitus type 1, eosinophilic fasciitis, gastrointestinal pemphigoid, Goodpasture's syndrome, Graves' disease, Guillain-Barré syndrome (GBS), Hashimoto's encephalopathy, Hashimoto's thyroiditis, Lupus erythematosus, multiple sclerosis, myasthenia gravis, *pemphigus vulgaris*, pernicious anaemia, polymyositis, primary biliary cirrhosis, psoriasis, psoriatic arthritis, relapsing polychondritis, rheumatoid arthritis, Sjögren's syndrome, transverse myelitis, ulcerative colitis, vasculitis, and Wegener's granulomatosis. Preferably, the autoimmune disease is multiple sclerosis. Among autoimmune diseases other than MS those, in which The components of the kit of the invention may therefore be for administration to a subject selected from the group consisting of a subject diagnosed with PML or a subject at risk of developing PML.

Subjects at risk of developing PML are well known in the state of the art. These subjects can be treated prophylactically with the proteins and peptides of the present invention. As outlined above, examples are patients who are immunodeficient or immunocompromised, e.g., due to an HIV infection or AIDS, or due to a tumor. Such patients may also have a congenital immunodeficiency, such as patients with idiopathic CD4+ lymphopenia or Hyper-IgE-Syndrome. Alternatively, the immune system may be compromised due to immunosuppressive treatment which is presently taking place or which is planned. Patients may be eligible for immunosuppressive treatment e.g., if they have an autoimmune disease, e.g., multiple sclerosis, rheumatoid arthritis, lupus erythematodes, Crohn's disease or psoriasis, or if they are transplantation patients, i.e. patients having received a transplant or about to receive a transplant. Any patient with acquired or congenital state of reduced immunity, in particular of compromised CD4+ T cell numbers and function, are potentially at risk to develop PML and subsequent PML-IRIS, if the underlying immunocompromise were to be corrected.

In the context of the invention, immunosuppressive treatment may be treatment e.g., with cyclosporin or FK506 binding protein, with cytotoxic drugs (e.g. cyclophosphamide, mitoxantron, busulphan and many others that are in standard use as single drug- or combination therapy in the treatment of hematologic or solid tumors) or with an immunosuppressive or immunomodulatory antibody, e.g., a monoclonal antibody selected from the group comprising natalizumab, efalizumab, rituximab, ocrelizumab and alemtuzumab. Immunosuppressive treatment may also be irradiation or chemotherapy.

The immunosuppressive treatment preferably comprises treatment of the subject with one or more immunosuppressive antibodies, more preferably one or more monoclonal antibodies or other biologic, cell therapy or small molecule-based treatments. It has been shown that immunosuppressive treatment, e.g., with several major monoclonal antibodies that are in use in cancer and autoimmune diseases including natalizumab (anti-VLA-4), efalizumab (anti-leukocyte function-associated antigen-1) already withdrawn from the market), rituximab (anti-CD20), ocrelizumab (anti-CD20), alemtuzumab (anti-CD52) or infliximab (anti-tumor necrosis factor (TNF)-alpha) or with the IgG1-TNF receptor 2 fusion protein etanercept may lead to PML and/or PML-IRIS. This risk may be prevented or reduced by means of the invention. It is anticipated that other biologicals or small molecules, e.g. the sphingosine-phosphate receptor 1 agonist, fingolimod, that compromise certain immune functions such as migration of activated immune cells into the CNS (during CNS immune surveillance), as is the case for natalizumab, or trap cells in secondary lymphoid organs, as is the case for fingolimod, and others with similar effects may lead to increased risk to develop PML/PML-IRIS. Accordingly, it is preferred that the subject to be treated by the peptides and proteins of the invention, either by prophylactic or therapeutic treatment, is a subject that is currently treated by one or more monoclonal antibodies selected from the group of natalizumab, efalizumab, rituximab, ocrelizumab and alemtuzumab or another immunosuppressive agent (see above), or a subject for whom such treatment is planned. Preferably, the subject is treated with the antibody natalizumab or a derivative thereof.

In a preferred embodiment, the invention relates to prophylactic or therapeutic vaccination which includes the administration of the VP1 protein or a protein having at least 70% amino acid identity with VP1, for example in the form of a pentamer or in the form of a VLP comprising or consisting of VP1 or a VP1 variant, to a subject which receives one or more of the above immunosuppressive antibodies, preferably natalizumab.

Treatment of a subject with the kit of the invention may be especially advantageous for a subject which has been diagnosed to be a carrier of JCV. However, there also is a significant risk of subjects being newly infected with JCV e.g. in the course of an immunosuppressive treatment. It is therefore also advantageous to immunize subjects to JCV by means of the inventive kit if no diagnosis of JCV infection is performed or if a test for JCV has been negative.

The components of the kit or the invention are preferably to be administered to a subject selected from the group of:
a) immunocompromised or immunodeficient subjects, such as carriers of HIV, subjects having immunosuppressive treatment or congenital immunodeficient patients such as patients with idiopathic CD4+ lymphopenia or Hyper-IgE-Syndrome;
b) subjects eligible for immunosuppressive treatment.

In one aspect, the present invention is directed to a pharmaceutical kit as described herein for use in treating PML, i.e. in treating a subject diagnosed with PML. As surprisingly shown by the inventors, immunity to JCV can be induced by means of the invention, JCV can be eliminated from the brain and the symptoms of PML may be healed (reduced or abolished).

The invention is also directed to a pharmaceutical kit as described herein for use in preventing PML and/or PML-IRIS in a subject selected from the group of:
a) immunocompromised or immunodeficient subjects, such as carriers of HIV, subjects having immunosuppressive treatment or congenital immunodeficient patients such as patients with idiopathic CD4+ lymphopenia or Hyper-IgE-Syndrome; and
b) subjects eligible for immunosuppressive treatment.

Immunosuppressive treatment may, e.g., be treatment of a subject diagnosed with an autoimmune disease or a transplantation patient. The components of the kit may be administered to said patient before, after or during immunosuppressive treatment. In particular if start of the immunosuppressive treatment is not pressing, it may be advantageous to start or to boost an immune response to JCV by means of the invention before immunosuppressive treatment is started. However, the inventors have shown that it is also possible to achieve an immune response to JCV sufficient to treat PML in an immunocompromised individual. This is a situation similar to subjects undergoing immunosuppressive treatment.

Under some circumstances, it may be advantageous to reduce or interrupt immunosuppressive treatment for the first days or weeks (e.g., 2 days, 5 days, 7 days, 14 days or 28 days after the immunisation or the invention, or until clearance of JCV from the brain is shown or the symptoms of PML healed. This may be decided by the medical practitioner depending on the immune status of the patient and the risks of reducing or interrupting the immunosuppressive treatment in the patient. Alternatively or additionally, an immune stimulatory treatment such as treatment with IL-7 can be administered to a subject.

The present invention is also directed to a method of treating PML and a method of preventing PML and/or PML-IRIS, wherein
a) a protein or peptide comprising at least one CD4+ epitope derived from JCV, wherein the epitope is selected from the group comprising SEQ ID NO: 1-92, is administered to a patient, and
b) optionally, an adjuvant selected from the group comprising a TLR-7 agonist and/or TLR-8 agonist is administered to a patient.

The invention is also directed to a protein or peptide comprising at least one CD4+ epitope derived from JCV, wherein the epitope is selected from the group comprising SEQ ID NO: 1-92. Said protein or peptide is one component of suitable the kit of the invention as described herein, and thus suitable for preparing said kit, adding adjuvant.

The present inventors have shown the biological relevance of the CD4+ epitopes disclosed, and have first isolated the peptides consisting of these epitopes. In the context of the invention, the epitopes may be presented in the context of MHC II with or without further processing by the antigen presenting cell, i.e., the term epitope relates to the amino acid sequence as disclosed in SEQ ID NO: 1-92, which was shown by the inventors to be able to induce a CD4+ T cell response, and not necessarily to the peptide which may be isolated from MHC II.

A protein or peptide comprising at least one CD4+ epitope derived from JCV, wherein the epitope is selected from the group comprising SEQ ID NO: 1-92, may be a fusion protein of VP1 or a protein having at least 70% amino acid identity with VP1, further comprising at least one epitope selected from the group comprising SEQ ID NO: 1 and SEQ ID NO: 46-76. The protein or peptide of the invention may thus comprise epitopes from more than one native JCV protein, e.g., from two, three or four JCV proteins.

As described above, the protein or peptide comprising at least one CD4+ epitope derived from JCV, wherein the epitope is selected from the group comprising SEQ ID NO: 1-92 may be employed for preparing the kit of the invention, i.e., for immunisation of a subject to JCV, e.g., for treating or preventing PML or PML-IRIS. Alternatively, the protein or peptide comprising at least one CD4+ epitope derived from JCV, wherein the epitope is selected from the group comprising SEQ ID NO: 1-92 may be used for diagnosing infection with JCV. In particular, it may be used for diagnosing PML, preferably, in context with other methods such as analysis of symptoms and/or MRI or the brain.

The protein or peptides described herein are highly suitable for use in a method of diagnosing an infection with JCV and/or for diagnosing PML. The present invention thus also relates to a method for diagnosing infection with JCV or for diagnosing PML, comprising contacting a sample from a subject with a protein or peptide comprising at least one CD4+ epitope derived from JCV, wherein the epitope is selected from the group comprising SEQ ID NO: 1-92.

In one embodiment, the method for diagnosing infection is carried out under conditions suitable for binding of antibodies from the sample to said protein or peptide. If binding of antibodies to the sample is detected, e.g., by means of an ELISA, the subject is infected with JCV or has been infected with JCV.

In a preferred embodiment, the characterisation of the protein or peptide of the invention as comprising CD4+ epitopes is exploited. The method for diagnosing infection may be carried out under conditions suitable for detecting a reaction of CD4+ T cells in the sample to the presence of the epitope/epitopes. For example, a proliferation assay for T cells, which may e.g., measure incorporation of 3H-Thymidin, incorporation of bromo-2'-deoxyuridine (BrdU) or an assay for expression of activation markers such as CD25 or one or more cytokines may be used. An ELISPOT assay may be used, but an ELISA assay, a scintillation assay or extracellular or intracellular FACS can also be suitable. An assay for CD4+ activation by the protein or peptide comprising the disclosed epitope/epitopes may provide additional information with regard to a JCV infection or the immune status of the subject when combined with a PCR test and/or a test for the presence of antibodies to JCV in a sample from the patient, or it may be used instead of such a test previously known in the state of the art.

In one embodiment, CD4+ T cell activation is tested, and the phenotype of the CD4+ T cell is analysed, e.g., Th1, Th2 or Th1/2 phenotype is determined. This can be carried out based on expression of cytokines as known in the state of the art, and/or based on expression of other differentiation markers such as transcription factors.

In the context of the invention, the sample to be analysed (and transformed by this analysis) preferably is a blood sample, a brain tissue sample such as a sample from brain parenchyma or a sample of cerebrospinal fluid (CSF) e.g., from a brain biopsy or a puncture, or derived therefrom. For example, if T cell activity is to be analysed, PBMC or T cells may be isolated from the blood or CSF by methods known in the art. The inventors have however shown that it is preferable to analyse T cell activity of T cells from a brain tissue such as brain parenchyma. If antibodies are to be analysed, serum may be used.

In a preferred embodiment of the invention, the subject or patient is human. Alternatively, the subject or patient can also be humanized animal such as a humanized mouse susceptible to infection with JCV in an experimental system. As the subject/patient is human, proteins referenced in this application, if not specifically mentioned otherwise, are also preferably human or of human origin. For example, IL-7 should be human IL-7 or a derivative thereof capable of binding to IL-7 receptor and mediating signalling thereof. It can be recombinant IL-7, e.g., in the form of a fusion protein. TLR are also human TLR.

The inventors, who recognized the importance of CD4+ responses in the immune response to JCV and in clearing the virus from the brain, mapped the immunogenic epitopes of the polyoma virus JC. Immunodominant peptides from three open reading frames of JCV were identified. The peptides of a set of overlapping peptides spanning all open reading frames of JCV including important variants within the major capsid protein were tested. The CD4+ T cell epitopes identified may be used for diagnostic examinations of JCV infectious status, but may also be used to vaccinate patients/controls, e.g. subjects who have weak immune response against JCV (constitutively or due to disease (e.g. AIDS, constitutive immunodeficiencies such as idiopathic CD4+ lymphopenia) or treatment (cancer therapy, monoclonal antibody therapy, e.g. natalizumab in MS, but others as well) and are at risk to develop or have already developed PML.

The inventors have mapped the fine specificity of CD4+ T cell epitopes for all JCV proteins. T cell cultures and T cell clones from a brain biopsy of a patient suffering from PML and PML-immune reconstitution inflammatory syndrome (PML-IRIS) were examined. Since this immune response is protective in the sense that it targets the most important epitopes of the virus and leads to its elimination and containing the infection, the mapping data from testing peripheral blood lymphocytes of healthy controls and multiple sclerosis (MS) patients, but particularly the data from characterizing the antigen fine specificity of brain-infiltrating T cells during PML-IRIS supports biological relevance and usefulness for diagnostic and vaccination/therapeutic purposes.

In the course of the invention, furthermore, an individual healing attempt was performed in a patient with idiopathic CD4+ lymphopenia, a rare constitutive immunodeficiency, who developed PML at the age of 64 years. In this patient, the inventors tested the circumstances if vaccination with the entire major capsid protein VP1 can under certain conditions boost the insufficient immune response against JCV to the point that JCV can be eliminated from the brain. The inventors vaccinated the patient by subcutaneous injection of recombinant VP1 protein combined with a dermally applied TLR7 agonist (imiquimod, Aldara) and recombinant i.v. IL-7 (Cytheris). The patient not only showed an in vitro proliferative response against JCV VP1 after only two vaccinations, but also reduced the serum JCV viral load to 0, began to show slight contrast enhancement by brain MRI imaging and slightly elevated CSF cell counts, and finally is clinically improving, which all support that the vaccination worked in vivo.

The following examples are meant to illustrate the invention, but not to limit its scope. All publications cited herein are herewith fully incorporated for all purposes.

LEGENDS

FIG. 1: a) PHA-expanded bulk mononuclear cell populations from the brain biopsy (left panel), CSF (second panel from left) and PBMC (third panel from left) as well as unmanipulated PBMC (right panel) were tested against JCV VP1/VLP protein and tetanus toxoid protein (TTx). Results show the mean SI±SEM. Note the different scales for the y-axis. b) Ex-vivo quantification of Th1-, Th2-, Th17- and Th1-2 cells in PHA-expanded CD4+ T cells from brain biopsy (left panels), CSF (second panels from left), PBMCs (third panels from left) and in unmanipulated PBMCs (right panels). Numbers represent the percentage of positive cells. Th1 were identified as CD4+ IFN-gamma+ IL-17A−/IL4−; Th17 cells as CD4+ IL-17A+ IFN-gamma−; Th2 as CD4+ IL-4+ IFN-gamma−, and Th1-2 as CD4+ IFN-gamma+ IL-4+.

Figure 2:
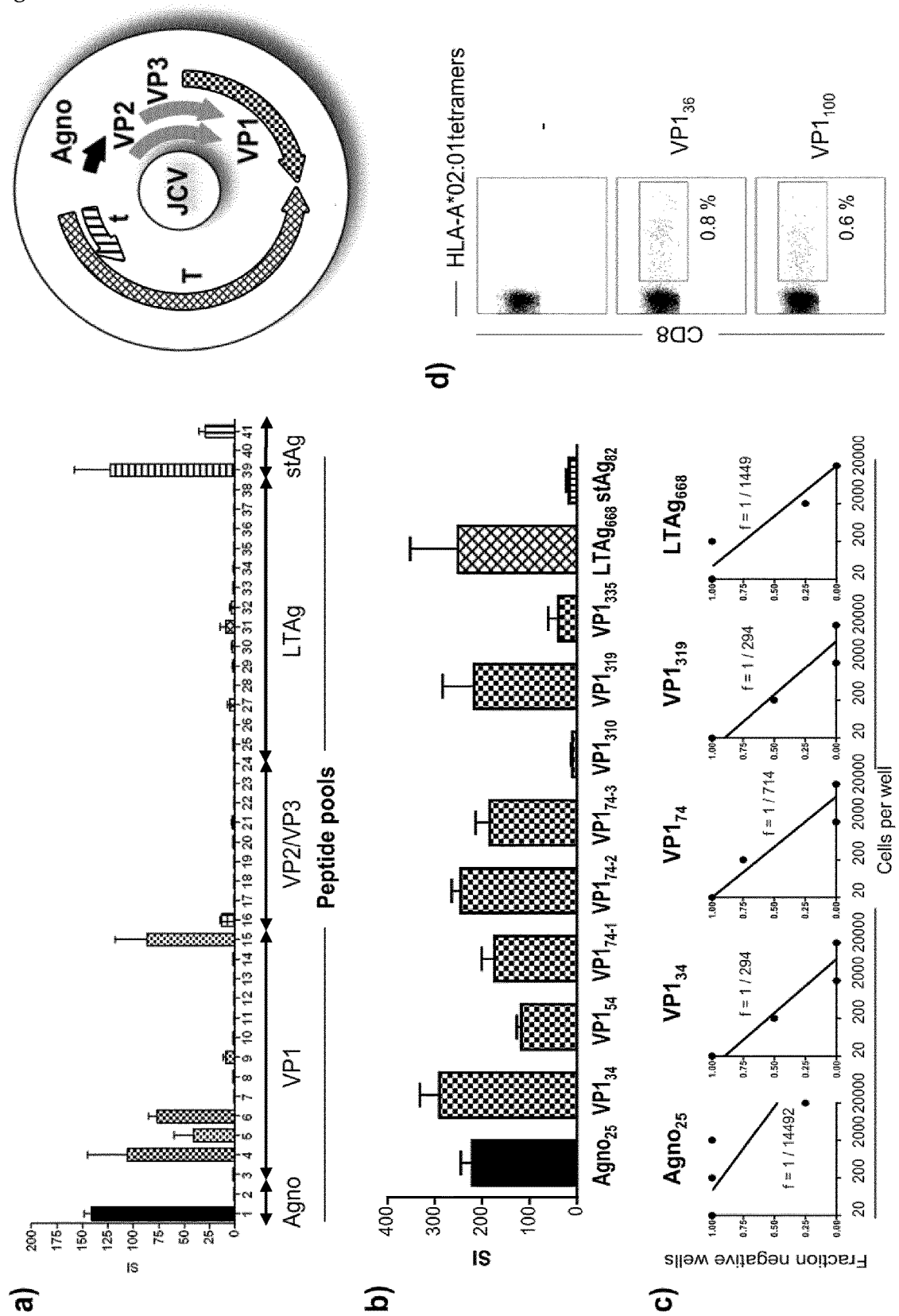

FIG. 2: a) Proliferative response of brain-derived PHA-expanded cells against 204 overlapping 15-mer peptides spanning all open reading frames of JCV (covering Agno, VP1, VP2, VP3, Large-T, and small-T proteins) and organized in 41 pools of 5 peptides each. Results show the mean SI±SEM. The different patterns of the bars correspond to the different open reading frames. Schematic representation of the 5 open reading frames in the JCV genome (upper right hand figure). b) Proliferative response of brain-derived bulk mononuclear cell populations against individual JCV peptides. Results show the mean SI±SEM. Note the different scales of the y-axes in panels a and b. c) Precursor frequency of T cells specific of the 5 JCV peptides inducing the strongest proliferative responses in PHA-expanded cells from brain biopsy. d) Percentage of CD8+ T cells that bind HLA-A*02:01-VP1$_{36}$ tetramers (middle graph) and HLA-A*02:01-VP1$_{100}$ tetramers (lower graph).

Figure 3:
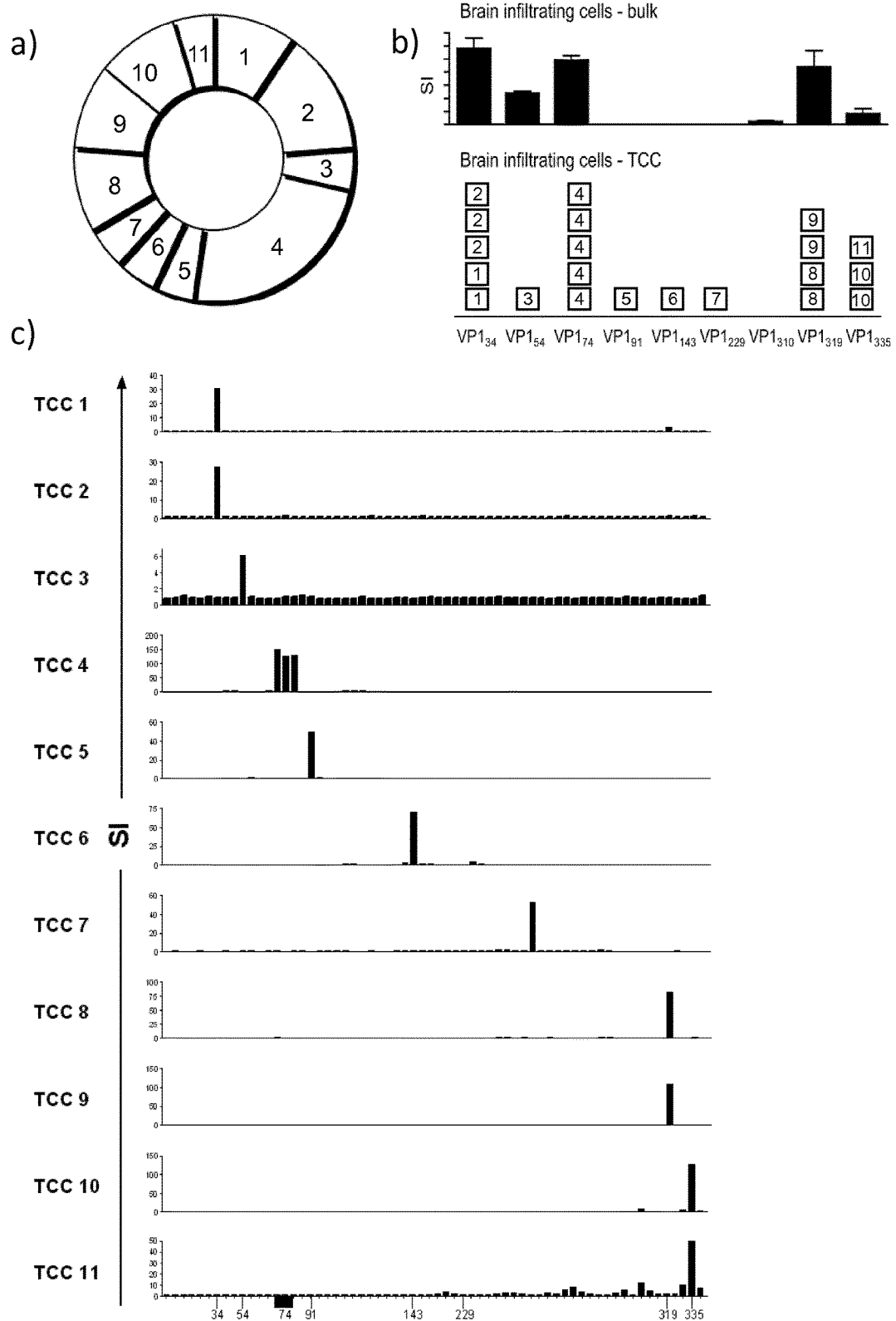

FIG. 3: a) Doughnut representing the frequency of each individual TCC in the brain biopsy. b) Proliferative response of TCC against 64 individual VP1 peptides. Results show the mean SI±SEM. c) Schematic representation of the immunodominant peptides identified for the brain-derived bulk population (upper graph, show the mean SI±SEM) and for the different TCC (lower graph the different patterns correspond to the different TCC and each single cell growing culture is represented by a square).

Figure 4:
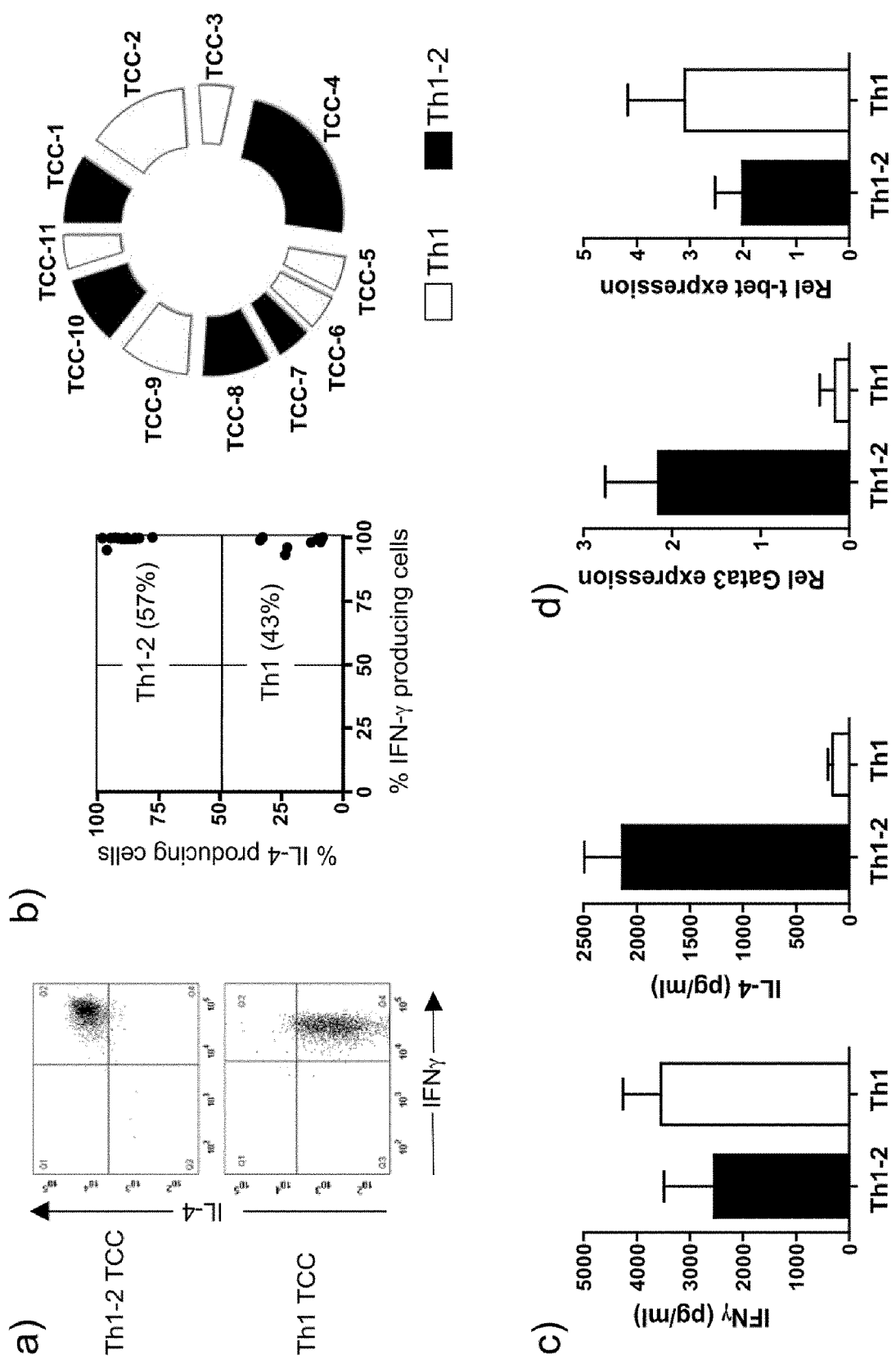

FIG. 4: a) Representative flow cytometry analysis of intracellular IFN-gamma and IL-4 production by a Th1-2 (upper plot) and a Th1 (lower plot) VP1/VLP-specific CD4+ T cell clone. b) The dot-plot represents the percentage of VP1-specific, brain-derived single cell cultures with Th1-2 and Th1 phenotype by intracellular cytokine staining Each dot corresponds to one of the 21 single cell cultures analyzed. The doughnut represents the functional phenotype of each TCC. c) ELISA detection of IFN-gamma and IL-4 production in culture supernatants of Th1-2 TCC (n=5, black bars) and Th1 TCC (n=6, white bars) 72 h after stimulation with PHA. Results show the mean±SEM. d) RT-PCR analysis for transcription factors Gata3 and t-bet of Th1-2 TCC (n=5, black bars) and Th1 TCC (n=6, white bars). Values are relative expression compared to brain-derived PHA-expanded cells (calibrator=1). Results show the mean±SEM.

FIG. 5 Treatment scheme for immunisation of an immunocompromised subject with VP1 M=month, D=day, W=week, MRI=Magnetic Resonance Imaging. Adjuvant (imiquimod) was administered directly after administration of VP1.

Figure 6:
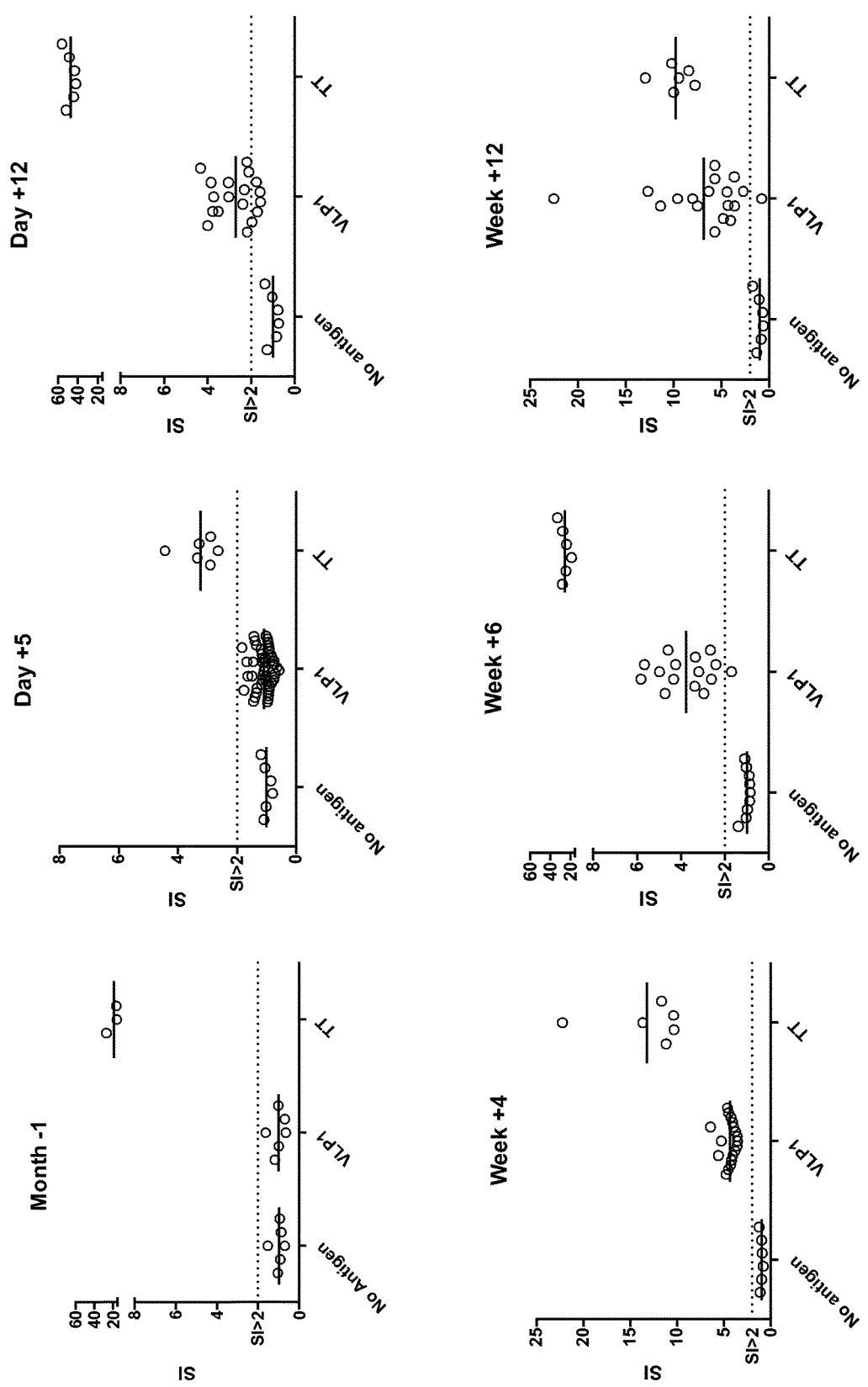
Figure 7A:
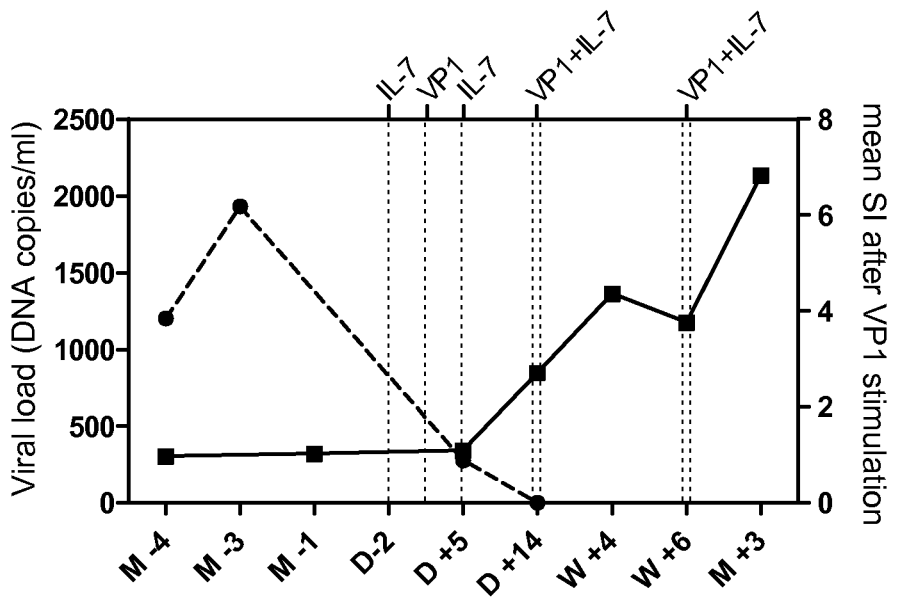
Figure 7B:
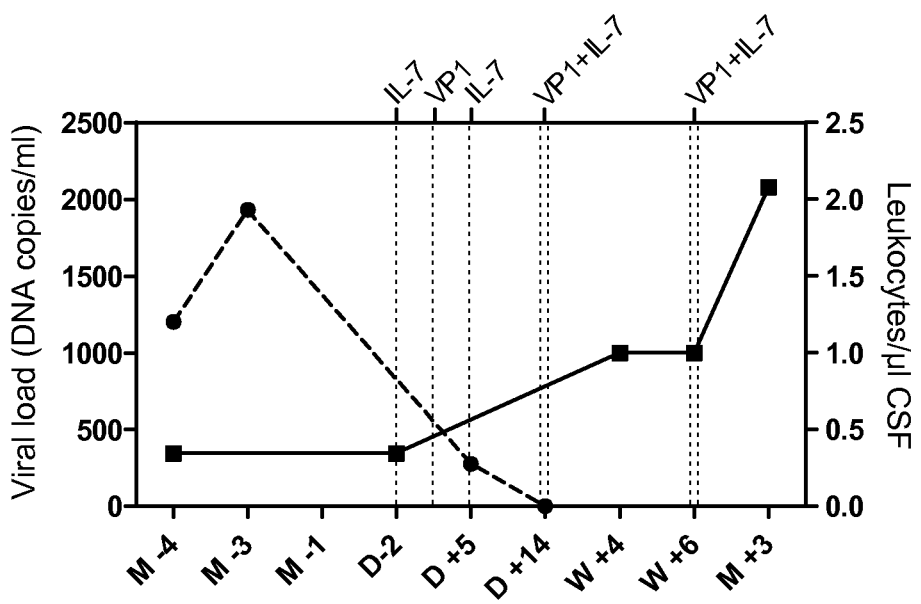

FIG. 6 Development of VP1 immune response during treatment VLP1=virus like particle1 composed of VP1 protein, TT=Tetanus toxoid FIG. 7 Course of Treatment FIG. 7A shows viral load and mean SI after VP1 stimulation, and FIG. 7B shows leukocyte counts in the CSF. Time points of administration of IL-7 and VP1 are identical and correspond to the scheme shown in FIG. 5.

Figure 8:
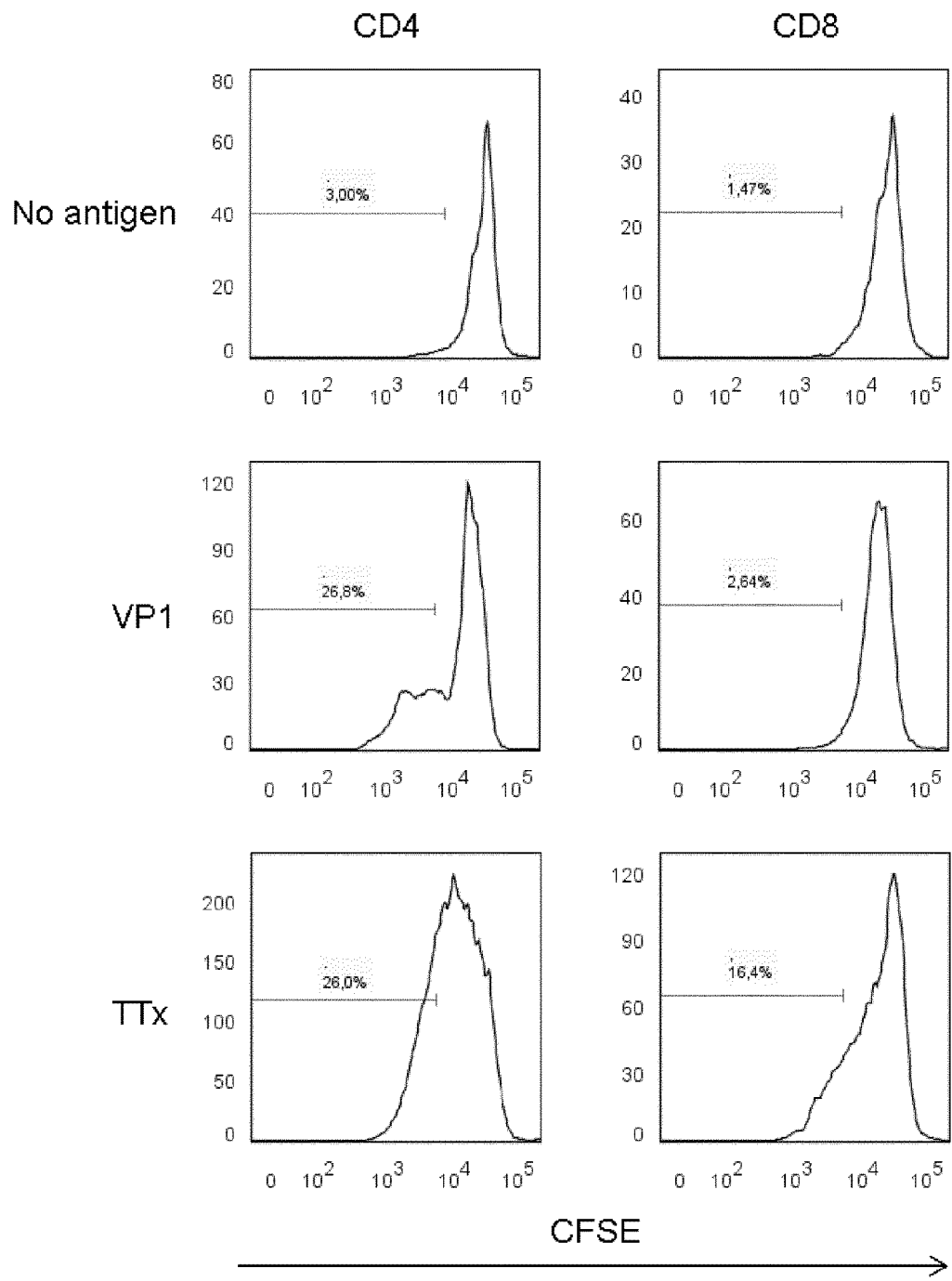

FIG. 8 Characterization of VP1-specific T-cells Only CD4+ cells proliferate after VP1 stimulus (6 weeks after immunization)

Figure 9:
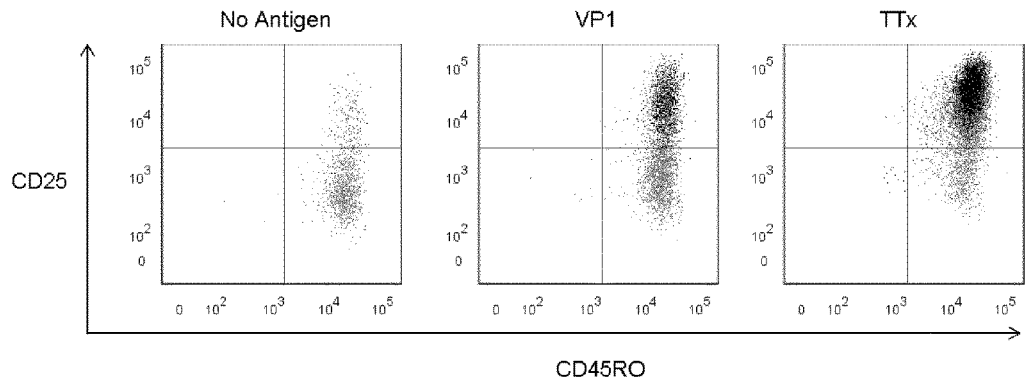

FIG. 9 Proliferating CD4 cells are activated memory cells

Figure 10:
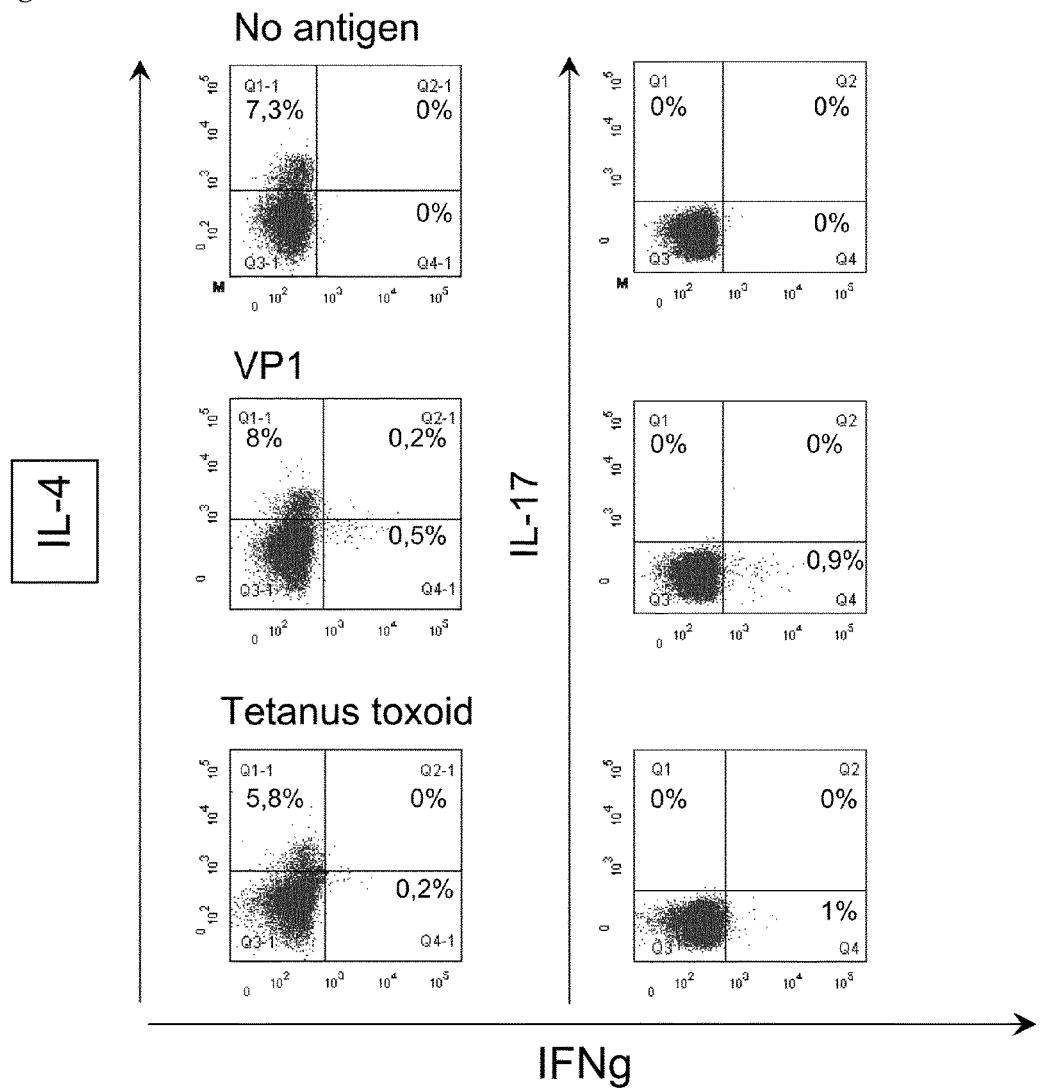

FIG. 10 CD4+ T cells activated by VP1 express a high background of IL-4 and produce IFN-gamma after VP1 stimulation. CD4+ T cells were stimulated with antigen on day 0. On day 6, they were restimulated with antigen, 1 hour later, secretion was blocked with Brefeldin A and after 15 h, an intracellular cytokine staining was performed and analysed by FACS.

FIG. 11 3H-thymidine incorporation assay At the time points indicated, peripheral blood mononuclear cells (PBMC) were obtained from the patients and freshly seeded (1×10e5 cells/well) with antigen (VP1/VLP). After 7 days of incubation, 3H-thymidine incorporation was measured. A stimulation index of >2 is considered a positive response. SIs are shown on the y-axis of the graph.

EXAMPLE 1—IDENTIFICATION OF IMMUNODOMINANT CD4+ EPITOPES

Material and Methods

Patients

HLA-class II types: DRB1*13:01, −*16:01; DRB3*02: 02; DRB5*02:02; DQA1*01:02, −*01:03; DQB1*05:02, −*06:03 (patient 1); and DRB1*11:03, −*15:01; DRB3*02: 02; DRB5*01:01; DQA1*01:02, −*05:XX (X indicating not typed to the exact subtype); DQB1*03:01, −*06:02 (patient 2).

Neuropathology

Small tissue fragments of a total volume of approximately 0.1 ml, were obtained by open biopsy. Following fixation in buffered formalin for 2 hours, tissue was embedded in paraffin. Microtome sections of 4 μm were stained with hematoxiline-eosin (H&E), van Gieson's trichrome, PAS, Turnbull's stain for siderin and Luxol. Immunohistochemical staining was performed on an automated Ventana HX IHC system, benchmark (Ventana-Roche Medical systems, Tucson, Ariz., USA) following the manufacturer's instructions using the following antibodies: anti-CD45/LCA (DAKO, Glostrup, Denmark; M701), anti-CD3 (DAKO; M1580), anti-CD45R0 (DAKO; M 0742), anti-CD20 (DAKO; M0755), anti-CD79a (DAKO; M7050), anti-CD68 (Immunotech/Beckmann-Coulter, Krefeld, Germany, 2164), anti-HLA-DR (DAKO; M775), anti-NF (Zymed/Invitrogen, Darmstadt, Germany, 80742971), anti-GFAP (DAKO; Z334) and anti-p53 (DAKO; M7001).

Brain Tissue Processing and Expansion of Brain-Derived, CSF-Derived and Peripheral Blood Mononuclear Cells A biopsy of approximately 0.033 ml was cut into small pieces and disrupted by incubation in a solution containing 1 mg/ml Collagenase A (Roche Diagnostics, Penzberg, Germany) and 0.1 mg/ml DNAse I (Roche) at 37° C. in a water bath for 45 min. The resulting cell suspension was washed three times, and brain-derived mononuclear cells were separated using a Percoll density gradient centrifugation (GE Healthcare, Munich, Germany). Cells were resuspended in a 30% Percoll solution and carefully underlayered with a 78% Percoll solution. After centrifugation brain-derived mononuclear cells were gathered from the interface of the gradient.

CSF-derived mononuclear cells were obtained directly from a diagnostic spinal tap, and peripheral blood mononuclear cells were separated by Ficoll density gradient centrifugation (PAA, Pasching, Austria).

Brain-, CSF- and peripheral blood-derived mononuclear cells were expanded in 96-well U-botton microtiter plates by seeding 2000 cells per well together with 2×10⁵ non-autologous, irradiated PBMC (3,000 rad) and 1 μg/ml of PHA-L (Sigma, St Louis, Mo.). Medium consisted of RPMI (PAA) containing 100 U/ml penicillin/streptomycin (PAA), 50 µg/ml gentamicin (BioWhittaker, Cambrex), 2 mM L-glutamine (GIBCO, Invitrogen) and 5% heat-decomplemented human serum (PAA). After 24 h, 20 U/ml of human recombinant IL-2 (hrIL-2, Tecin, Roche Diagnostics) were added and additional hrIL2 was added every 3-4 days. After two weeks cells were pooled and analyzed, cryopreserved or restimulated again with 1 µg/ml PHA, 20 U/ml hrIL-2 and allogeneic irradiated PBMC.

Flow Cytometry Analysis of Brain-Derived Mononuclear Cells

Brain-derived mononuclear cells directly from brain digestion were stained with the following antibodies for surface markers: CD45 (AmCyan, 2D1, BD Pharmingen, San Diego, USA), CD56 (Alexa 488, B159, BD Pharmingen), CD3 (PeCy7, UCHT1, eBioscience, San Diego, USA), CD4 (APC, RPA-T4, eBioscience), CD8 (PB, DK25, Dako, Glostrup, Denmark), CD45RO (FITC, UCHL1, eBioscience), CD19 (FITC, HIB19, BD Pharmingen), CD38 (APC, HIT2, BD Pharmingen), and CD27 (APC-Alexa 750, CLB-27/1, Invitrogen). Analysis was performed on a3 LSRII (BD Biosciences, Heidelberg, Germany) flow cytometer.

Proteins and Peptides

For the identification of JCV-specific T cells, 204 (13-16 mer) peptides covering the entire JC viral proteome were applied. Peptides were synthesized and provided by pe (peptides and elephants GmbH, Potsdam, Germany). These 204 peptides overlap by 5 amino acids and include 35 common single amino acid mutations. To account for amino acid variations, that occur among the different JCV genotypes and strains, amino acid sequences of each JCV encoded protein including Agno, VP1, VP2, VP3, Large T antigen and small t antigen from all 479 JCV genomic sequences available in GenBank (by March 2008) were aligned and those polymorphisms, which were prevalent in more than 1% of the all retrieved sequences, were defined as common mutations.

In order to determine which individual peptides are recognized by CNS-derived T cells, a two-dimensional seeding scheme was applied. Peptides were arranged in a set of 82 pools, where each pool contains 5 different peptides. By the combination of different peptides in each well according to a rectangular matrix and each individual peptide appearing in exactly two pools, in which the residual peptides differ, immunogenic candidate peptides could be identified at the intersections of the positive pools.

JCV VP1 protein forms virus-like (VLP) particles, and VP1 and VLP are therefore used as interchangeable terms. VP1 protein forming VLP (VP1/VLP) was generated by the Life Science Inkubator, Bonn, Germany, as previously described (Goldmann et al., 1999). 20 mer myelin peptides with an overlap of 10 amino acids and covering MBP (16 peptides), MOG (25 peptides) and PLP (27 peptides) were synthesized and provided by PEPScreen, Custom Peptide Libraries, SIGMA. Tetanus toxoid (TTx) (Novartis Behring, Marburg, Germany) was used as positive control.

Proliferative Assays

Recognition of JCV Peptides, VP1/VLP and TTx was tested by seeding duplicates in 96-well U-botton microtiter plates 2-2.5×10$^4$ brain-derived, CSF-derived or peripheral blood-derived PHA-expanded cells per well and 1×10$^5$ autologous irradiated PBMC with or without peptides for 72 hours. Unmanipulated PBMC were tested at 2×10$^5$ cells/well in a 7-day primary proliferation. In addition to TTx, PHA-L stimulation was added as positive control. All JCV peptides were either tested in pools or as individual peptides at a final concentration of 2 µM per peptide for peptides in pools and at a concentration of 10 µM for individual peptides. VP1/VLP was tested at 2 µg/ml, Tetanus toxoid (TTx) at 5 µg/ml and PHA at 1 µg/ml. Proliferation was measured by $^3$H-thymidine (Hartmann Analytic, Braunschweig, Germany) incorporation in a scintillation beta counter (Wallac 1450, PerkinElmer, Rodgau-Jürgesheim, Germany). The stimulatory index (SI) was calculated as SI=Mean cpm (counts per minute)(peptide)/Mean cpm (background). Responses were considered as positive when SI>3, cpm>1000 and at least three standard deviations (SD) above average background cpm. Myelin peptides were tested as individual peptides at 5 µM as described above.

Generation of Brain-Derived VP1/VLP-Specific T Cell Clones 2.5×10$^4$ brain-derived PHA-expanded cells were seeded in 96-well U-botton microtiter plates with 1×10$^5$ autologous irradiated PBMC with or without VP1/VLP protein. After 48 hours of culture, plates were split into mother and daughter plates. Proliferation was measured in daughter plates by methyl-$^3$H-thymidine incorporation. VP1/VLP-responsive cultures were identified in mother plates, and IL-2 was added every 3-4 days until day 12. T cell clones (TCC) were established from positive cultures by seeding cells from VP1/VLP-responsive wells under limiting dilution conditions at 0.3 and 1 cell/well in 96-well U-botton microtiter plates, and addition of 2×10$^5$ allogeneic, irradiated PBMC and 1 µg/ml of PHA-L in complete RPMI. After 24 h, 20 U/ml of human recombinant IL-2 were added. VP1/VLP specificity was then confirmed seeding 2.5×10$^4$ cells from growing colonies with autologous irradiated PBMC with or without VP1/VLP protein for 72 h. Specific cultures were restimulated every two weeks with 1 µg/ml PHA-L, 20 U/ml hrIL-2 and allogeneic irradiated PBMC, and hrIL2 was added every 3-4 days.

TCR Analysis

TCR Vβ chain expression was assessed in PHA-expanded cells and T cell clones by 22 anti TCRBV monoclonal antibodies (Immunotech, Marseille, France, (Muraro et al., 2000)) in combination with CD4 (APC, eBioscience) and CD8 (PB, PB, DakoCytomation, Denmark).

Determination of Precursors Frequency in CNS-Derived Mononuclear Cells

Frequencies of VP1/VLP-specific cells were determined by limiting dilution. 20, 200, 2.000 or 20.000 brain-derived PHA-expanded cells were seeded in quadruplicates in 96-well U-botton microtiter plates with 1×10$^5$ autologous irradiated PBMC with or without VP1/VLP protein. After 72 hours, proliferation was measured by methyl-$^3$H-thymidine incorporation. Frequencies were calculated as previously described (Taswell, 1981). Observed data were: r, the number of negatively responding cultures or wells of each dose i; n, the total number of wells per dose i, and X, the number of cells in the dose i. Calculated data was: pi=ri/ni, the fraction of negatively responding cultures of each dose i. The frequency was calculated using the following formula: f=−(ln pi)/λi.

Cytokine Production

For intracellular cytokine staining, PHA-expanded cells and TCC were analyzed 12 days after last restimulation. Cells were stimulated with PMA (50 ng/ml, Sigma) and ionomycin (1 µg/ml, Sigma) in the presence of Brefeldin A (10 µg/ml, eBioscience) for 5 h. Next, cells were stained with LIVE/DEAD® Fixable Dead Cell Stain Kit (AmCyan, Molecular Probes, Invitrogen), fixed and permeabilized with the corresponding buffers (eBioscience), and stained for CD3 (PE, DakoCytomation, Denmark), CD8 (PB, DakoCytomation, Denmark), IFNgamma (FITC, BDPharmingen), IL-4 (PE-Cy7, eBioscience) and IL-17A (Alexa Fluor®-647, eBioscience) at room temperature. IFN-gamma-, IL-4- and IL-2 levels were also determined by ELISA following the manufacturer's protocol (Biosource, Camarillo, Calif.) in culture supernatants of PHA-expanded cells and in TCC 72 hours after stimulation with PHA or VP1/VLP.

Quantification of mRNA Expression Levels by RT-PCR

For mRNA gene expression assays, the primer and probe sets (Tbet, Hs00203436_m1 and Gata3, Hs00231122_m1) were purchased from Applied Biosystems (Foster City, Calif.). 18S rRNA was used as endogenous control, and the relative gene expression was calculated by the ΔΔCt method using brain-derived PHA-expanded cells as calibrator.

ELISA for VP1/VLP-Specific Antibodies

The titer of VP1/VLP-specific immunoglobulin G antibodies in CSF and sera from both IRIS-PML patients was determined as described previously (Weber et al., 1997). Briefly, ELISA plates were coated with 100 ml VP1-VLP (1 mg/ml) and incubated with serial dilutions of CSF or sera. Human IgG was captured by a biotin conjugated anti-human Fc antibody (eBioscience) and detected by an avidin horseradish peroxidase (eBioscience). Antibody titers in CSF as well as serum were adjusted to the total amount of IgG in the particular compartment. Results were expressed as arbitrary units, which were standardized using always the same human serum as standard.

HLA-A*0201/JCV $VP1_{36}$ and $VP1_{100}$ Tetramers and Tetramer Staining

HLA-A*02:01 tetrameric complexes were synthesized as previously described. Briefly HLA-A*02:01, β2 microglubluin and epitope peptide were refolded and isolated using size eclusion chromatography. Site-specific biotinylation was achieved through addition of the BirA target sequence to the last C terminal extracellular domain of the HLA-A*0201 molecule. Tetrameric complexes were generated using Extravidin-PE (Sigma). PHA-expanded brain-infiltrating cells were stimulated with anti-CD2/CD3/CD28 MACs beads (Miltenyi Biotec, Auburn, Calif.) and at day 5 after stimulation cells were washed and resuspended to a concentration of $5 \times 10^6$ cells/ml. 100 µl were stained with 3 µl of PE-coupled tetrameric HLA-A*02:01/JCV $VP1_{36}$ or HLA-A*02:01/JCV $VP1_{100}$. After 30 min incubation at 37° C. the cells were washed and stained with anti-CD3 (PB, eBiolegend, San Diego, Calif.) and anti-CD8 (FITC, Dako) for additional 30 min on ice. Then cells were washed and fixed with 0.5% paraformaldehyde before analysis by flow cytometry.

Results

Two Cases of Natalizumab-Associated PML-IRIS

Two male patients of 41 and 43 years with relapsing-remitting MS (RR-MS) presented July 2009 and January 2010 respectively with clinical signs (visual field defect in patient 1; monoparesis in patient 2) and imaging findings suspicious of PML after 28- and 40 months respectively of natalizumab treatment. Natalizumab was stopped immediately, and several rounds of plasmapheresis performed. Both patients subsequently developed PML-IRIS with patchy or band-like areas of contrast enhancement on MRI (FIG. 1a) and worsened clinical findings of complete loss of vision in patient 1, and hemiplegia, hemianopia and neuropsychological deterioration in patient 2. With respect to diagnostic workup, patient 1 was immediately diagnosed as PML based on CSF JCV viral load, although it was low. Diagnosis in patient 2 was more complicated with repeatedly negative PCR results for CSF JCV viral load until the third testing was positive just above threshold levels; 12 copies; threshold 10 copies in the NIH reference laboratory). In contrast to the low or borderline JCV CSF viral loads, antibody testing for JCV major capsid protein (VP1/VLP)-specific antibodies in serum and CSF, which was established during this study, revealed strong intrathecal antibody response with 95-180-fold higher VP1/VLP-specific antibody titers in the CSF compared to serum after adjusting total IgG concentrations to the same levels. Hence, different from the PCR testing for viral DNA, the intrathecal antibody response left no doubt of CNS infection by JCV at the time of PML-IRIS. The analysis of the IgG subclasses in patient 2 demonstrated that intrathecal antibodies are mainly IgG1 and IgG3. These data indicate a strong JCV-specific humoral immune response that is confined to the CNS compartment and directed primarily against the major structural JCV protein VP1/VLP. Whether minor components of the antibody response target other JCV proteins remains to be studied.

Due to the above difficulties to diagnose PML, patient 2 underwent a diagnostic brain biopsy to confirm or refute PML. Neuropathological examination failed to show the typical signs of PML, i.e. nuclear inclusions in hyperchromatic oligodendrocytes and bizarre astrocytes, but rather a paucity of CNS cells and massive perivascular and parenchymal lymphomononuclear infiltrates, reactive gliosis with stellate astrocytes and predominance of diffuse and destructive parenchymal infiltrates of foamy macrophages. The majority of cells stained positive for HLA-DR, which is usually exclusively found on activated microglia and absent in normal brain tissue. T cells and B cells were present in the infiltrate, and a high proportion of the latter stained positive for the plasma cell marker CD138. Part of the biopsy tissue was processed, and CNS-derived mononuclear cells were also characterized by flow cytometry. 96.5% of cells expressed the pan hematopoietic cell marker CD45 (not shown) and among them 42.4% expressed the pan T cell marker $CD3^+$. Of these 24.1% were $CD8^+$ and 70.4% $CD4^+$ T cells. Almost all of these cells expressed the memory marker CD45RO. 29% of $CD45^+$ CNS-infiltrating cells expressed the B cell marker CD19, and among these 86.1% were positive for CD27/CD38, i.e. they were memory B cells/plasma cells. Accordingly, a diagnosis of inflammatory demyelinating disease rather than PML was made. Subsequent immunohistochemistry for JCV was negative, but sparse nuclear signals for JCV DNA were found by the second attempt of in situ hybridization (data not shown), which together with the low JCV viral load and strong intrathecal antibody response confirmed the initial suspicion of PML and pointed at IRIS rather than the underlying demyelinating disease as responsible for the neuropathological findings.

Antigen Specificity of Brain-Infiltrating T Cells

Next the antigen specificity and frequency of brain-infiltrating T cells were characterized. Brain-derived mononuclear cells were first expanded as bulk populations by an unbiased stimulus (PHA). While our culture conditions favored the expansion of $CD4^+$ over $CD8^+$ T cells the relative composition of $CD4^+$ T cells remained stable as demonstrated by staining with monoclonal antibodies against T cell receptor (TCR) variable chains V131-V1322. Due to the almost threefold excess of memory $CD4^+$ over $CD8^+$ T cells at the time of brain biopsy, we focused our attention on $CD4^+$ cells and assessed their specificity for JCV. For this purpose, expanded brain T cells were tested against recombinant JCV capsid protein VP1/VLP and against tetanus toxin protein (TTx) in proliferative assays. We directly compared brain-derived versus CSF- or peripheral blood-derived T cells as well as versus unmanipulated peripheral blood mononuclear cells. As shown in FIG. 1a, brain-derived T cells responded with a stimulation index (SI)>600 against VP1/VLP protein with no response against TTx. SIs against VP1/VLP and TTx in the CSF were 7 and 14 respectively, and in PHA-expanded PBMC the responses to VP1/VLP and TTx were negative and moderately positive (SI of 6.5) respectively. Unmanipulated PBMC showed a significantly stronger response to TTx compared to VP1/VLP in a 7 days primary proliferation assay.

Functional Phenotype of Brain-Infiltrating CD4+ T Cells

The inventors then examined if intracerebral CD4+ T cells belonged to one of the major T helper (Th) subtypes, Th1, Th2 or Th17 cells, based on their cytokine secretion pattern. Expanded bulk T cell populations from the brain, CSF and PBMC as well as unmanipulated PBMC were examined by intracellular cytokine staining against IFN-gamma, IL-4, and IL-17, the signature cytokines of Th1-, Th2- and Th17 cells. IL-17-producing cells were hardly detectable (FIG. 1b), while IFN-gamma-secreting cells made up between 46.1 and 53.2% in cells from the brain and CSF (FIG. 1b). When combining intracellular staining for IFN-gamma and IL-4, the situation was remarkably different. In the brain and CSF-derived population, Th1-, Th2- and bifunctional Th1-2 cells (secreting both IL-4 and IFN-gamma) were similar in frequency (FIG. 1b), while Th2 cells predominated in the peripheral blood-derived, PHA-expanded cells (FIG. 1b). 32.7% of brain-derived CD4+ T cells had a bifunctional Th1-2 phenotype.

Fine Specificity and Frequency of Brain-Infiltrating T Cells

To determine which specific JCV peptides are recognized by brain-infiltrating T cells, 204 15-mer peptides spanning all JCV proteins (Agno, VP1, VP2, VP3, Large-T, and small-T) were synthesized and arranged in a set of 82 pools, where each peptide appears twice, but in two different pools (see methods). Brain-derived T cells responded to multiple pools (FIG. 2a; pools 1-41). The inventors identified 15 immunogenic candidate peptides that were then tested individually and lead to the identification of 11 stimulatory peptides (peptides with SI>10) (FIG. 4b). The response was directed against peptides 4 (Agno$_{25}$, the number denotes the first amino acid (aa) of the 15-mer peptide), 20 (VP1$_{34}$), 23 (VP1$_{54}$), 27-29 (VP1$_{74}$)(all VP1$_{74}$ peptides; 28 and 29 are variants of peptide 27 with single aa mutations), 72 (VP1$_{310}$), 73 (VP1$_{319}$), 76 (VP1$_{335}$), 191 (LTAg$_{668}$), and 195 (sTAg$_{82}$) (peptides with SI>25 in bold). Thus, brain-derived T cells responded to several JCV proteins (Agno, VP1, LTAg, sTAg), however, by far the strongest against VP1 (6 peptides). That VP1 is the prime target is supported by an even stronger response against entire VP1/VLP protein (FIG. 1a) and by the higher precursor frequencies of VP1-specific T cells (between 1/294 and 1/714 T cells responding to peptides VP1$_{34}$, VP1$_{319}$ and VP1$_{74}$) when compared to cells responding to Agno$_{25}$ (1/14492) and LTAg$_{668}$ (1/1449) (FIG. 2c). When the inventors examined PHA-expanded CSF- and peripheral blood-derived T cells, CSF only mounted weak responses against pool 39 and peptide LTAg$_{668}$ contained in this pool, and PBMC were negative. Remarkably, peptide VP1$_{34}$, the peptide that elicits the strongest response with respect to SI (FIG. 2b) and precursor frequency (FIG. 2c), contains the JCV epitope VP1$_{36}$, one of the two epitopes together with VP1$_{100}$ that are recognized by HLA-class I-restricted CD8+ T cells in the context of HLA-A*02:01 (Du Pasquier et al., 2003b). PML-IRIS patient 2 is HLA-A*02:01+ (HLA-class I and -class II types under methods), for this reason the inventors determined the frequency of CD8+ T cells specific of these two HLA-A*02:01 JCV epitopes in the PHA-expanded brain-infiltrating CD8+ T cells by tetramer staining 0.8% of PHA-expanded brain-infiltrating CD8+ T were specific for VP1$_{36}$ and 0.6% for VP1$_{100}$ (FIG. 4d). With respect to HLA-class II, patient 2 expresses the MS-associated HLA-DR haplotype DRB1*15:01 and DRB5*01:01. The JCV-specific CD4+ T cell response was largely restricted by DRB1*15:01/B5*01:01, when VP1/VLP protein was presented by APCs from a DRB1*15:01/B5*01:01 homozygous donor (not shown). These data demonstrate that, similar to intrathecal antibodies, the CD4+ T cell response is mainly directed against the major structural JCV protein VP1 and that peptide VP1$_{34}$ contains an epitope for both virus-specific CD4+ and CD8+ T cells. Such a focus of CD4+ and CD8+ T cells on the same immunodominant epitope has previously been shown for an influenza nucleoprotein peptide (Carreno et al., 1992).

Table 1 shows the immunodominant CD4+ T cell epitopes identified by the inventors.

Since PML is characterized by oligodendrocyte lysis and release of myelin and since the patient suffers from MS, it was of interest to examine if brain-derived T cells responded to myelin proteins. PHA-expanded brain-derived T cells were tested against overlapping peptides spanning the major myelin proteins, myelin basic protein (MBP), proteolipid protein (PLP), and myelin oligodendrocyte glycoprotein (MOG), but none of the myelin peptides was recognized despite a strong response against JCV VP1/VLP protein.

TABLE 1

List of immunodominant JCV epitopes.

| Peptide # | Name (position) | Sequence | Length | SEQ ID NO |
|---|---|---|---|---|
| 4 | *Agno (25-39)* | AQRILIFLLEFLLDF | 15 | 1 |
| 20 | *VP1 (34-48)* | VDSITEVECFLTPEM | 15 | 2 |
| 23 | *VP1 (54-68)* | HLRGFSKSISISDTF | 15 | 3 |
| 24 | VP1 (64-78) V1 | ISDTFESDSPNRDML | 15 | 4 |
| 25 | VP1 (64-78) V2 | ISDTFESDSPNFDML | 15 | 5 |
| 26 | VP1 (64-78) V3 | ISDTFESDSPNKDML | 15 | 6 |
| 27 | *VP1 (74-88) V1* | NRDMPLCYSVARIPL | 15 | 7 |
| 28 | *VP1 (74-88) V2* | NFDMLPCYSVARIPL | 15 | 8 |

TABLE 1-continued

List of immunodominant JCV epitopes.

| Peptide # | Name (position) | Sequence | Length | SEQ ID NO |
|---|---|---|---|---|
| 29 | *VP1 (74-88) V3* | NKDMLPCYSVARIPL | *15* | *9* |
| 30 | VP1 (81-95) | YSVARIPLPNLNEDL | 15 | 10 |
| 31 | *VP1 (91-105)* | LNEDLTCGNILMWEA | *15* | *11* |
| 32 | VP1 (101-115) | LMWEAVTLKTEVIGV | 15 | 12 |
| 33 | VP1 (108-122) V1 | LKTEVIGVTSLMNVH | 15 | 13 |
| 34 | VP1 (108-122) V2 | LKTEVIGVTTLMNVH | 15 | 14 |
| 35 | VP1 (108-122) V3 | LKTEVIGVTALMNVH | 15 | 15 |
| 36 | VP1 (118-129) V1 | LMNVHSNGQATH | 12 | 16 |
| 37 | VP1 (118-129) V2 | LMNVHSNGQAAH | 12 | 17 |
| 38 | VP1 (118-129) V3 | LMNVHSNGQASH | 12 | 18 |
| 39 | VP1 (123-137) V1 | SNGQATHDNGAGKPV | 15 | 19 |
| 40 | VP1 (123-137) V2 | SNGQAAHDNGAGKPV | 15 | 20 |
| 41 | VP1 (123-137) V3 | SNGQASHDNGAGKPV | 15 | 21 |
| 42 | VP1 (133-147) | AGKPVQGTSFHFFSV | 15 | 22 |
| 43 | *VP1 (143-157)* | HFFSVGGEALELQGV | *15* | *23* |
| 44 | VP1 (151-165) V1 | ALELQGVLFNYRTKY | 15 | 24 |
| 45 | VP1 (151-165) V2 | ALELQGVLFNYRTTY | 15 | 25 |
| 46 | VP1 (161-175) V1 | YRTKYPDGTIFPKNA | 15 | 26 |
| 47 | VP1 (161-175) V2 | YRTTYPDGTIFPKNA | 15 | 27 |
| 48 | VP1 (161-175) V3 | YRTTYPHGTIFPKNA | 15 | 28 |
| 49 | VP1 (171-186) | FPKNATVQSQVMNTEH | 16 | 29 |
| 50 | VP1 (182-196) | MNTEHKAYLDKNKAY | 15 | 30 |
| 51 | VP1 (193-208) | KNKAYPVECWVPDPTR | 16 | 31 |
| 52 | VP1 (203-217) | PDPTRNENTRYFGTL | 15 | 32 |
| 53 | VP1 (210-224) | NTRYFGTLTGGENVP | 15 | 33 |
| 54 | VP1 (220-234) V1 | GENVPPVLHITNTAT | 15 | 34 |
| 55 | VP1 (220-234) V2 | GENVPSVLHITNTAT | 15 | 35 |
| 56 | VP1 (220-234) V3 | GENVPPVLHITKTAT | 15 | 36 |
| 57 | *VP1 (229-243) V1* | ITNTATTVLLDEFGV | *15* | *37* |
| 58 | *VP1 (229-243) V2* | ITKTATTVLLDEFGV | *15* | *38* |
| 59 | VP1 (239-253) V1 | DEFGVGPLCKGDNLY | 15 | 39 |
| 60 | VP1 (239-253) V2 | DEFGVRPLCKGDNLY | 15 | 40 |
| 61 | VP1 (249-263) | GDNLYLSAVDVCGMF | 15 | 41 |
| 62 | VP1 (259-273) V1 | VCGMFTNRSGSQQWR | 15 | 42 |
| 72 | *VP1 (310-321)* | RVDDGQPMYGMDAQV | *15* | *43* |
| 73 | *VP1 (319-331)* | MAQVEEVRVFEGTE | *14* | *44* |
| 76 | *VP1 (335-349)* | GDPDMMRYVDKYGQL | *15* | *45* |

TABLE 1-continued

List of immunodominant JCV epitopes.

| Peptide # | Name (position) | Sequence | Length | SEQ ID NO |
|---|---|---|---|---|
| 78 | VP2 (1-15) | MGAALALLGDLVATV | 15 | 46 |
| 79 | VP2 (11-24) | LVATVSEAAAATGF | 14 | 47 |
| 80 | VP2 (20-34) | AATGFSVAEIAAGEA | 15 | 48 |
| 81 | VP2 (30-43) | AAGEAAATIVEIA | 14 | 49 |
| 82 | VP2 (39-51) | EVEIASLATVEGI | 13 | 50 |
| 83 | VP2 (47-61) | TVEGITSTSEAIAAI | 15 | 51 |
| 84 | VP2 (57-71) | AIAAIGLTPETYAVI | 15 | 52 |
| 85 | VP2 (67-81) | TYAVITGAPGAVAGF | 15 | 53 |
| 86 | VP2 (77-88) | AVAGFAALVQTV | 12 | 54 |
| 87 | VP2 (84-97) | LVQTVTGGSAIAQL | 14 | 55 |
| 153 | LTAg (328-342) | FADSKNQKSICQQAV | 15 | 56 |
| 154 | LTAg (338-351) | CQQAVDTVAAKQRV | 14 | 57 |
| 155 | LTAg (347-361) | AKQRVDSIHMTREEM | 15 | 58 |
| 156 | LTAg (357-370) | TREEMLVERFNFLL | 14 | 59 |
| 158 | LTAg (376-390) | IFGAHGNAVLEQYMA | 15 | 60 |
| 159 | LTAg (386-399) | EQYMAGVAWIHCLL | 14 | 61 |
| 161 | LTAg (405-419) | VIYDFLKCIVLNIPK | 15 | 62 |
| 162 | LTAg (415-429) | LNIPKKRYWLFKGPI | 15 | 63 |
| 168 | LTAg (472-486) | VFEDVKGTGAESRDL | 15 | 64 |
| 169 | LTAg (482-495) | ESRDLPSGHGISNL | 14 | 65 |
| 170 | LTAg (491-506) | GISNLDCLRDYLDGSV | 16 | 66 |
| 171 | LTAg (500-514) | DYLDGSVKVNLERKH | 15 | 67 |
| 172 | LTAg (508-522) | VNLERKHQNKRTQVF | 15 | 68 |
| *191* | *LTAg (668-681)* | *CTFHICKCFQCFKK* | *14* | *69* |
| *195* | *StAg (82-96) V1* | *VGCDFPPNSDTLYCK* | *15* | *70* |
| *196* | *StAg (82-96) V2* | *VSCDFPPNSDTLYCK* | *15* | *71* |
| 200 | StAg (123-137) | RKFLRSSPLVWIDCY | 15 | 72 |
| 201 | StAg (133-146) | WIDCYCFDCFRQWF | 14 | 73 |
| 202 | StAg (142-156) | FRQWFGCDLTQEALH | 15 | 74 |
| 203 | StAg (149-162) | DLTQEALHCWEKVL | 14 | 75 |
| 204 | StAg (158-172) | WEKVLGDTPYRDLKL | 15 | 76 |
| 271 | VP1 L55F (54-68) | HFRGFSKSISISDTF | 15 | 77 |
| 272 | VP1 S269Y (259-273) | VCGMFTNRSGYQQWR | 15 | 78 |
| 273 | VP1 K60N (54-68) | HLRGFSNSISISDTF | 15 | 79 |
| 274 | VP1 D66H (54-68) | HLRGFSKSISISHTF | 15 | 80 |
| 275 | VP1 D66H (64-78) | ISHTFESDSPNRDML | 15 | 81 |
| 276 | VP1 V223I (220-234) | GENIPPVLHITNTAT | 15 | 82 |

TABLE 1-continued

List of immunodominant JCV epitopes.

| Peptide # | Name (position) | Sequence | Length | SEQ ID NO |
|---|---|---|---|---|
| 277 | VP1 N265D (259-273) | VCGMFTDRSGSQQWR | 15 | 83 |
| 278 | VP1 S267F (259-273) | VCGMFTNRFGSQQWR | 15 | 84 |
| 279 | VP1 Q271H (259-273) | VCGMFTNRSGSQHWR | 15 | 85 |
| 280 | VP1 S61L (54-68) | HLRGFSKLISISDTF | 15 | 86 |
| 281 | VP1 K60E (54-68) | HLRGFSESISISDTF | 15 | 87 |
| 282 | VP1 N265H (259-273) | VCGMFTHRS The inventors' data provide novel insights into this subject and lead them to propose the following pathogenetic events during PML-IRIS under natalizumab treatment. The anti-VLA-4 antibody inhibits immune surveillance of JCV infection at immunoprivileged sites such as the brain by blocking cell migration (Stuve et al., 2006) and local antigen presentation in the CNS (del Pilar Martin et al., 2008). As a result, pathologic neurotropic JCV variants may lead to PML in a small number (1/500-1/1000) of treated MS patients for reasons that are not yet understood (Major, 2010; Ransohoff, 2005). As soon as PML is suspected and natalizumab is stopped or actively removed by plasmapheresis, fully functional and activated T cells regain access to the CNS compartment, initiate the strong inflammation that is typical for PML-IRIS and effectively eliminate virus-infected cells by a number of mechanisms including CD4+ and CD8+ T cells and antibody-forming plasma cells.

TABLE 2

Characterization of VP1 specific brain infiltrating T cell clones (TCC)

| TCC # | Well # | Th Phenotype | TCR Vbeta | Fine specificity |
|---|---|---|---|---|
| TCC-1 | 17A | Th0 | Vβ2 | $VP1_{34}$ |
|  | 18A | Th0 | Vβ2 | $VP1_{34}$ |
| TCC-2 | 16A | Th1 | Vβ2 | $VP1_{34}$ |
|  | 28A | Th1 | Vβ2 | $VP1_{34}$ |
|  | 18B | Th1 | Vβ2 | $VP1_{34}$ |
| TCC-3 | 29A | Th1 | Vb18 | $VP1_{54}$ |
| TCC-4 | 10A | Th0 | Vβ5.1 | $VP1_{74-1}, VP1_{74-2}, VP1_{74-3}$ |
|  | 14A | Th0 | Vβ5.1 | $VP1_{74-1}, VP1_{74-2}, VP1_{74-3}$ |
|  | 27A | Th0 | Vβ5.1 | $VP1_{74-1}, VP1_{74-2}, VP1_{74-3}$ |
|  | 30A | Th0 | Vβ5.1 | $VP1_{74-1}, VP1_{74-2}, VP1_{74-3}$ |
|  | 19B | Th0 | Vβ5.1 | $VP1_{74-1}, VP1_{74-2}, VP1_{74-3}$ |
| TCC-5 | 3A | Th1 | Vβ— | $VP1_{91}$ |
| TCC-6 | 11B | Th1 | Vβ— | $VP1_{143}$ |
| TCC-7 | 12B | Th0 | Vβ2 | $VP1_{229}$ |
| TCC-8 | 21A | Th0 | Vβ— | $VP1_{319}$ |
|  | 25A | Th0 | Vβ— | $VP1_{319}$ |
| TCC-9 | 36A | Th1 | Vβ— | $VP1_{319}$ |
|  | 1B | Th1 | Vβ— | $VP1_{319}$ |
| TCC-10 | 19A | Th0 | Vβ5.3 | $VP1_{335}$ |
|  | 3B | Th0 | Vβ5.3 | $VP1_{335}$ |
| TCC-11 | 24A | Th1 | Vβ— | $VP1_{335}$ |

Among the CNS-infiltrating T- and B cells, CD4+ T cells with either Th1- or the above bifunctional Th1-2 phenotype are probably the most critical element based on the following findings. Their parallel secretion of Th1-(IFN-gamma) and Th2 (IL-4) cytokines probably explains the expression of HLA-class II molecules on resident cells such as virus-infected astrocytes and microglia, but also on infiltrating immune cells, since IFN-gamma is the strongest inducer of HLA-class II. Although colocalization studies of HLA-DR with an astrocytic marker such as GFAP could not be performed due the paucity of material, the widespread expression of HLA-DR strongly suggests that these are also positive. In analogy to MS and its animal model experimental autoimmune encephalitis (EAE), where local reactivation of immigrating T cells has been demonstrated, JCV-specific Th1-2 and also Th1 cells are probably locally reactivated by recognition of JCV peptides on JCV-infected, HLA-class II positive astrocytes, microglia/macrophages or recruited dendritic cells (DCs). Furthermore, the secretion of large quantities of IL-4 leads to activation and expansion of memory B cells/plasmablasts in the CNS compartment with the consequence of virus-specific antibody secretion. Locally produced JCV capsid protein (VP1)-specific IgG antibodies may recognize virus-infected oligodendrocytes, which could then be lysed by complement- or antibody-mediated cellular cytotoxicity. The relative increase in the CSF of IgG1 and IgG3 antibodies, which bind complement with high affinity and have been described in the context of other viral infections, supports this notion. Since infected oligodendrocytes do not express HLA-class II, but effectively express HLA-class I, it can be expected that JCV-specific, HLA-A2-restricted CD8+ cytolytic T cells (Koralnik et al., 2001) (Koralnik et al., 2002) also contribute by killing JCV-infected oligodendrocytes and/or astrocytes. That these previously described cells in the peripheral blood of AIDS patients with PML are probably also participating in the local eradication of JCV in the brain is supported by our observation of CD8+ T cells specific for JCV $VP1_{36}$ and JCV $VP1_{100}$ as defined by peptide-loaded HLA-A*02:01 tetramers. Infected astrocytes may not only serve as local antigen presenting cells for CD4+ virus-specific T cells, but may also be killed by Th1-2 cytolytic cells (Hemmer et al., 1997), but this together with the question of DR expression by astrocytes will require further studies.

The above pathogenetic scenario accounts for the effects of IFN-gamma- and IL-4, i.e. the widespread expression of HLA-class II molecules in the brain as well as the strong intrathecal antibody response against JCV, however, it is still puzzling that a large fraction of brain-infiltrating cells show a Th1-2 phenotype. Previously, these cells were referred to as Th0 cells and considered an intermediate differentiation step before naive cells develop into memory cells committed to either Th1 or Th2 lineage (Mosmann and Coffman, 1989). This notion has, however, already been contended early based on following the cytokine patterns of single clones (Kelso, 1995). Today, Th1- and Th2 cells are understood as mutually exclusive fates (Ansel et al., 2006). However, individual TCC with dual cytokine secretion have been described as Th0 cells in measles virus infection (Howe et al., 2005) and among disease-exacerbating autoreactive T cells during altered peptide ligand-based therapy of MS (Bielekova et al., 2000). The inventors' present observation of stable Th1-2 clones based on intracellular cytokine staining, cytokine secretion and transcription factor expression point to a defined T helper cell subpopulation in the CNS rather than an intermediate or transient differentiation stage. Due to the abovementioned ill-defined role of Th0 cells and the prior controversy about their existence as terminally differentiated cells, we propose here to refer to IFN-gamma/IL-4 T helper cells as bifunctional Th1-2 cell. The context and signals that lead to this Th1-2 differentiation need further examination. In a recently published study in a viral infection model, the authors demonstrated that non-protective Th2 cells could be converted to stably IFN-gamma/IL-4-expressing and protective CD4+ cells by concerted action of antigen-specific TCR signal, type I and -II interferons and IL-12 (Hegazy et al., 2010) (Zhu and Paul, 2010). The inventors' findings are the first evidence for the existence of a stable GATA-3+ T-bet+ and IL-4+IFN-gamma+ Th2+1 phenotype in vivo in humans. It is conceivable that these cells were reprogrammed in the brain, and they could well explain the unusually strong immune response and fulminant course of PML-IRIS.

Regarding the fine specificity of brain-infiltrating T cells, the inventors' data are interesting in several aspects. The JCV-specific T cell response is overall broad since peptides from almost all JCV proteins are recognized, which is consistent with the inventors' efforts to map immunodominant epitopes of JCV for peripheral blood-derived CD4+ T cells in healthy donors and MS patients. However, more than 50% of peptides recognized by brain-derived CD4+ T cells are part of the major structural protein VP1. Furthermore, VP1-specific T cells dominate with respect to strength of proliferation and precursor frequency. It is intriguing that $VP1_{34-48}$ contains not only a major epitope for cytotoxic, HLA-A*02:01-restricted $CD8^+$ T cells (Du Pasquier et al., 2003b), which the inventors found as well in the brain of the PML-IRIS patients by tetramer staining, but also for HLA-DRB1*15:01/DRB5*01:01-restricted $CD4^+$ T cells. Furthermore, the recognition of peptide $VP1_{74}$ and two variants thereof with single amino acid substitutions indicates that recognition of this epitope may be relevant to protect the host from immune evasion during persistent JCV infection. This has been shown previously for human immunodeficiency—(Borrow et al., 1997) and lymphocytic choriomeningitis virus infections (Ciurea et al., 2001). The vigorous intrathecal antibody response against VP1 further underscores the role of this structural protein. Therefore, the inventors' findings show that VP1 is important for protective immune responses against JCV-infected brain cells and that these are mediated by antibodies, $CD4^+$ and $CD8^+$ T cells. The strength of this response is probably in part determined by the HLA type of patient 2, who expresses both the major MS risk allele DRB1*15:01/DRB5*01:01 and A*02:01, which present an identical VP1 epitope to $CD4^+$ and $CD8^+$ T cells. He may therefore have experienced a particularly pronounced T cell-mediated immune response in the brain with its immunopathologic consequences of massive PML-IRIS, brain swelling, and neurological worsening. As already pointed out by others (Cinque et al., 2003) the JCV-specific immune response is a double-edged sword. Without a functional immune response brain cells are lysed by uncombated viral infection. On the other hand, if unleashed, the vigorous JCV-specific response during PML-IRIS causes brain inflammation and edema, and while it effectively eliminates JCV from the CNS, it may lead to death of the patient if not at least temporarily attenuated by immunosuppression (Tan et al., 2009b).

The cellular and humoral JCV-specific immune response in the brain during PML-IRIS not only complicates the treatment, but may also cloud the diagnosis of PML in the first place. Different from current routine, which relies on CSF JCV viral load and, if a biopsy is performed, on immunohistochemistry and in situ hybridization for JCV antigen and DNA respectively, the intrathecal antibody response against VP1 appears more robust and should be examined. In both PML-IRIS patients of this study intrathecal VP1-specific antibody titers were extremely high despite almost undetectable JCV DNA by PCR and in situ hybridization. The important role of JCV antibody testing is supported by prior observations of high antibody titers in AIDS patients with PML (Weber et al., 1997), but also recent data in natalizumab-treated MS patients (Gorelik et al., 2010).

Another important and unexpected observation of this study is that, different from the JCV-specific antibody response, pathogenetically relevant T cells are confined to the CNS parenchyma itself, and that the CSF is of little use for investigating T cell specificity and function. This finding is probably highly relevant not only to PML-IRIS, but also to MS, where most studies have focused on CSF as a surrogate for the responses within the CNS from obvious reasons, i.e. because CNS tissue is rarely available to investigators. Future research should therefore make every possible effort to examine biopsy or autopsy tissue if it can be acquired. When studying the brain-infiltrating CD4+ T cells of this MS patient with PML-IRIS, the inventors were further surprised to see that none of the peptides from three major myelin proteins were recognized, suggesting that bystander activation or—recruitment of myelin-specific T cells during massive brain inflammation does not occur, but that cells are exquisitely specific for the causal agent.

EXAMPLE 2—IMMUNISATION TO JCV

An individual healing attempt was performed in a patient with idiopathic CD4+ lymphopenia, a rare constitutive immunodeficiency, who developed PML at the age of 64 years (referred to as "patient Hamburg" in FIG. 11). The male patient had been healthy, i.e. not experienced unusual or frequent infections, throughout his life, and in February 2010 was hospitalized with signs of an encephalitis of unknown origin. He was thoroughly worked up, and a diagnosis of suspected EBV-related encephalitis was made. Following transient improvement during antiviral therapy, he deteriorated further albeit slowly. During 2010, two brain biopsies were performed, and in the second one at the end of 2010, a diagnosis of progressive multifocal leukoencephalopathy (PML) was made based on positive JCV viral load in the CSF and on demonstration of JCV-infected oligodendrocytes and astrocytes in the brain. In parallel, the inventors found a low CD4+ T cell count (around 300/ microliter) as well as a CD4+/CD8+ ratio of 0.5 or less, which are both consistent with the diagnosis of idiopathic CD4+ lymphopenia. In addition, in vitro experiments in the laboratory documented an absent T cell response to JCV virus VP1 in peripheral blood mononuclear cells and an almost complete absence of naïve CD4+ T cells. Following these observations, the inventors reasoned that the patient probably had developed PML based on a pre-existing and probably genetically determined low CD4+ number, which became further accentuated by entirely physiological immune involution, which sets in and increases above 50 years of age.

The inventors wanted to test if vaccination with VP1, and, in this case of CD4+ lymphopenia, preferably combined with recombinant IL-7, would increase the number of JCV-specific T cells that the patients must have had, since he is JCV-positive. Further, if this were to occur, the inventors hoped that the vaccine-induced or -boosted JCV VP1-specific T cell response would lead to these cells' migrating to the CNS and elimination of virus and virus-infected cells from the CNS compartment. The inventors therefore applied for an "individual healing attempt", discussed this option and its potential risks with the patient and obtained his consent. The use of IL-7 (Cytheris) was further supported by a recent publication in another case of CD4+ lymphopenia (Patel et al., 2010), in whom recombinant IL-7 together with antiviral drugs had led to substantial improvement of the patient, however, in that patient, no immunological studies were performed, and therefore nothing was known about improvement of antigen-specific immune responses.

The vaccination approach in the above patient included the following steps (for timing of vaccinations and tests see scheme below): Subcutaneous injection with the entire recombinant major capsid protein VP1 (provided by the Life Science Inkubator, Bonn) in combination with a dermally applied TLR7 agonist (imiqimod, Aldara; commercially available) and i.v. recombinant IL-7 (Cytheris). The VP1 protein was administered in the form of virus-like particles (VLP), as the recombinantly expressed VP1 protein associated to such particles under the conditions used herein. As shown below, the patient not only showed an in vitro proliferative response against JCV VP1 after only two vaccinations, but also reduced the JCV viral load to 0 and finally began to show slight contrast enhancement around the PML lesions by brain MRI imaging, which all support that the vaccination worked in vivo. He also showed clinical improvement with slight delay after developing a JCV-specific immune response. Furthermore, since the inventors' data from the brain-infiltrating T cells in the PML-IRIS patient described in Example I suggested that JCV-specific CD4+ T cells with a T helper 1-2 phenotype are probably crucial for elimination of JCV virus from the brain, the inventors also stained for Th1-2 CD4+ T cells in the cerebrospinal fluid of the patient, and could demonstrate that these cells are indeed present.

Another individual healing attempt was performed in a patient with breast cancer who received chemotherapy and developed acute myeloid leukaemia (AML) as a side effect of the chemotherapy. The patient then received an autologous and allogeneic hematopoietic stem cell transplant as treatment of the AML and subsequently developed acute graft-versus-host disease (grade IV). The immunodeficiency acquired as a consequence of these treatments resulted in PML. This case is referred to as "patient Zurich" in FIG. 11. Both patients were treated by recombinant IL-7 (s.c.). 2 days later, the first dose of VP1 (s.c. 1 mg, imiquimod cream on the skin) was administered. 2 days after the first dose of VP1, the second dose of rIL-7 was given.

On day 12 after the first IL-7 dose, the patients received a second vaccination with VP1 s.c. plus imiquimod, and in this case simultaneously rIL-7. At week 6, a third dose of VP1/imiquimod and a fourth dose of rIL-7 were administered. FIG. 11 shows the results from the below described proliferation assay performed at the time points indicated in the graph with peripheral blood mononuclear cells (PBMC) obtained from both patients. A stimulation index of >2 is considered a positive response. It can be seen that both patients showed a positive immune response against JCV after vaccination.

Material and Methods

Blood and CSF Samples

Biological samples were obtained after informed written consent. Peripheral blood mononuclear cells (PBMCs) were separated from EDTA-blood by Ficoll (PAA, Pasching, Austria) density centrifugation.

Cerebrospinal fluid (CSF)-derived mononuclear cells were expanded by seeding 2000 cells/well plus $2 \times 10^5$ irradiated (45 Gy) allogeneic feeder cells. 1 µg/ml PHA-L (Sigma-Aldrich, Munich, Germany) and 500 IU/ml IL-2 (kindly provided by Federica Sallusto, Institute for Research in Biomedicine, Bellinzona, CH) was added. The addition of IL-2 was repeated every 3-4 days until day 14.

Proliferation Assays

The proliferation response of PBMC to VP1 (kindly provided by Viktorya Demina, Life Science Inkubator, Bonn, Germany) and Tetanus toxoid (TTx, Novartis, Marburg, Germany) was tested by seeding $2 \times 10^5$ cells in a 96-well U-bottom microtiter plates. VP1 was used at 2 µg/ml and TTx at 5 µg/ml. After 7 days incubation, incorporation of $^3$H-thymidine (Hartmann Analytic, Braunschweig, Germany) was measured. Stimulatory indices (SI) were calculated by dividing the mean CPM (counts per minute) of the wells plus antigen by the mean CPM of the wells without antigen.

To measure proliferative responses to VP1 and TTx by flow cytometry the CellTrace™ CFSE Cell Proliferation Kit (Invitrogen, Darmstadt, Germany) was used. Therefore, cells were seeded as described above and restimulated with antigen after six days and treated with CFSE following the manufacturer's instruction. After five days cells were analysed by flow cytometry.

Flow Cytometry Analysis

Whole blood stainings were performed by adding the appropriate antibody cocktail in a volume of 50 µl to 100 µl blood. The mixture was incubated for 30 minutes at room temperature, followed by 10 minutes of red blood cell lysis with FACS Lysing Solution (BD PharMingen). After washing, the cells were analysed by flow cytometry in a LSR II (BD). Following antibodies were used: CD4 (APC, RPA-T4, eBioscience), CD8 (PB, DK25, Dako, Glostrup, Denmark), CD45RO (FITC, UCHL1, eBioscience), CD25 (PE-Cy7, eBioscience), CD3 (PE, DakoCytomation, Denmark), CD8 (PB, DakoCytomation, Denmark), IFN-gamma (FITC, BDPharmingen), IL-4 (PE-Cy7, eBioscience).

REFERENCES

Anonymous. http://tysabri.de/index.php?inhalt=tysabri.pmlinzidenz 2011.

Astrom K E, Mancall E L, Richardson E P, Jr. Progressive multifocal leuko-encephalopathy; a hitherto unrecognized complication of chronic lymphatic leukaemia and Hodgkin's disease. Brain 1958; 81: 93-111.

Carreno B M, Turner R V, Biddison W E, Coligan J E. Overlapping epitopes that are recognized by CD8+ HLA class I-restricted and CD4+ class II-restricted cytotoxic T lymphocytes are contained within an influenza nucleoprotein peptide. J Immunol 1992; 148: 894-9.

Cavacini L A, Kuhrt D, Duval M, Mayer K, Posner M R. Binding and neutralization activity of human IgG1 and IgG3 from serum of HIV-infected individuals. AIDS Res Hum Retroviruses 2003; 19: 785-92.

Cinque P, Bossolasco S, Brambilla A M, Boschini A, Mussini C, Pierotti C, et al. The effect of highly active antiretroviral therapy-induced immune reconstitution on development and outcome of progressive multifocal leukoencephalopathy: study of 43 cases with review of the literature. J Neurovirol 2003; 9 Suppl 1: 73-80.

Du Pasquier R A, Clark K W, Smith P S, Joseph J T, Mazullo J M, De Girolami U, et al. JCV-specific cellular immune response correlates with a favorable clinical outcome in HIV-infected individuals with progressive multifocal leukoencephalopathy. J Neurovirol 2001; 7: 318-22.

Du Pasquier R A, Corey S, Margolin D H, Williams K, Pfister L A, De Girolami U, et al. Productive infection of cerebellar granule cell neurons by JC virus in an HIV+ individual. Neurology 2003a; 61: 775-82.

Du Pasquier R A, Kuroda M J, Schmitz J E, Zheng Y, Martin K, Peyerl F W, et al. Low frequency of cytotoxic T lymphocytes against the novel HLA-A*0201-restricted JC virus epitope VP1(p36) in patients with proven or possible progressive multifocal leukoencephalopathy. J Virol 2003b; 77: 11918-26.

Du Pasquier R A, Kuroda M J, Zheng Y, Jean-Jacques J, Letvin N L, Koralnik I J. A prospective study demonstrates an association between JC virus-specific cytotoxic T lymphocytes and the early control of progressive multifocal leukoencephalopathy. Brain 2004a; 127: 1970-8.

Du Pasquier R A, Schmitz J E, Jean-Jacques J, Zheng Y, Gordon J, Khalili K, et al. Detection of JC virus-specific cytotoxic T lymphocytes in healthy individuals. J Virol 2004b; 78: 10206-10.

Du Pasquier R A, Stein M C, Lima M A, Dang X, Jean-Jacques J, Zheng Y, et al. JC virus induces a vigorous CD8+ cytotoxic T cell response in multiple sclerosis patients. J Neuroimmunol 2006; 176: 181-6.

Egli A, Infanti L, Dumoulin A, Buser A, Samaridis J, Stebler C, et al. Prevalence of polyomavirus BK and JC infection and replication in 400 healthy blood donors. J Infect Dis 2009; 199: 837-46.

Gillespie S M, Chang Y, Lemp G, Arthur R, Buchbinder S, Steimle A, et al. Progressive multifocal leukoencephalopathy in persons infected with human immunodeficiency virus, San Francisco, 1981-1989. Ann Neurol 1991; 30: 597-604.

Goldmann C, Petry H, Frye S, Ast O, Ebitsch S, Jentsch K D, et al. Molecular cloning and expression of major structural protein VP1 of the human polyomavirus JC virus: formation of virus-like particles useful for immunological and therapeutic studies. J Virol 1999; 73: 4465-9.

Hegazy A N, Peine M, Helmstetter C, Panse I, Frohlich A, Bergthaler A, et al. Interferons direct Th2 cell reprogramming to generate a stable GATA-3(+)T-bet(+) cell subset with combined Th2 and Th1 cell functions. Immunity 2010; 32: 116-28.

Houff S A, Major E O, Katz D A, Kufta C V, Sever J L, Pittaluga S, et al. Involvement of JC virus-infected mononuclear cells from the bone marrow and spleen in the pathogenesis of progressive multifocal leukoencephalopathy. N Engl J Med 1988; 318: 301-5.

Jilek S, Jaquiery E, Hirsch H H, Lysandropoulos A, Canales M, Guignard L, et al Immune responses to JC virus in patients with multiple sclerosis treated with natalizumab: a cross-sectional and longitudinal study. Lancet Neurol 2010; 9: 264-72.

Kleinschmidt-DeMasters B K, Tyler K L. Progressive multifocal leukoencephalopathy complicating treatment with natalizumab and interferon beta-1a for multiple sclerosis. N Engl J Med 2005; 353: 369-74.

Koralnik I J. Progressive multifocal leukoencephalopathy revisited: Has the disease outgrown its name? Ann Neurol 2006; 60: 162-73.

Koralnik I J, Du Pasquier R A, Kuroda M J, Schmitz J E, Dang X, Zheng Y, et al. Association of prolonged survival in HLA-A2+ progressive multifocal leukoencephalopathy patients with a CTL response specific for a commonly recognized JC virus epitope. J Immunol 2002; 168: 499-504.

Koralnik I J, Du Pasquier R A, Letvin N L. JC virus-specific cytotoxic T lymphocytes in individuals with progressive multifocal leukoencephalopathy. J Virol 2001; 75: 3483-7.

Langer-Gould A, Atlas S W, Green A J, Bollen A W, Pelletier D. Progressive multifocal leukoencephalopathy in a patient treated with natalizumab. N Engl J Med 2005; 353: 375-81.

Major E O. Progressive multifocal leukoencephalopathy in patients on immunomodulatory therapies. Annu Rev Med 2010; 61: 35-47.

Ogg G S, Jin X, Bonhoeffer S, Dunbar P R, Nowak M A, Monard S, et al. Quantitation of HIV-1-specific cytotoxic T lymphocytes and plasma load of viral RNA. Science 1998; 279: 2103-6.

Padgett B L, Walker D L, ZuRhein G M, Eckroade R J, Dessel B H. Cultivation of papova-like virus from human brain with progressive multifocal leucoencephalopathy. Lancet 1971; 1: 1257-60.

Patel A, Patel J, Ikwuagwu J. A case of progressive multifocal leukoencephalopathy and idiopathic CD4+ lymphocytopenia. J. Antimicrob. Chemother. 2010; 65:2489.

Ransohoff R M. Natalizumab and PML. Nat Neurosci 2005; 8: 1275.

Stoner G L, Ryschkewitsch C F, Walker D L, Webster H D. JC papovavirus large tumor (T)-antigen expression in brain tissue of acquired immune deficiency syndrome (AIDS) and non-AIDS patients with progressive multifocal leukoencephalopathy. Proc Natl Acad Sci USA 1986; 83: 2271-5.

Stuve O, Marra C M, Jerome K R, Cook L, Cravens P D, Cepok S, et al Immune surveillance in multiple sclerosis patients treated with natalizumab. Ann Neurol 2006; 59: 743-7.

Tan C S, Dezube B J, Bhargava P, Autissier P, Wuthrich C, Miller J, et al. Detection of JC virus DNA and proteins in the bone marrow of HIV-positive and HIV-negative patients: implications for viral latency and neurotropic transformation. J Infect Dis 2009a; 199: 881-8.

Tan K, Roda R, Ostrow L, McArthur J, Nath A. PML-IRIS in patients with HIV infection: clinical manifestations and treatment with steroids. Neurology 2009b; 72: 1458-64.

Weber T, Trebst C, Frye S, Cinque P, Vago L, Sindic C J, et al. Analysis of the systemic and intrathecal humoral immune response in progressive multifocal leukoencephalopathy. J Infect Dis 1997; 176: 250-4.

Zhu J, Paul W E. CD4+ T cell plasticity-Th2 cells join the crowd. Immunity 2010; 32: 11-3.

Zhu J, Yamane H, Paul W E. Differentiation of effector CD4 T cell populations (*). Annu Rev Immunol 2010; 28: 445-89.

Zonios D I, Falloon J, Bennett J E, Shaw P A, Chaitt D, Baseler M W, et al. Idiopathic CD4+ lymphocytopenia: natural history and prognostic factors. Blood 2008; 112: 287-94.

Zurhein G, Chou S M. Particles Resembling Papova Viruses in Human Cerebral Demyelinating Disease. Science 1965; 148: 1477-9.

DE 195 43 553

Goldmann et al., 1999, Journal of Virology 73, p. 4465-4469

---

The invention claimed is:

1. A method of treating progressive multifocal leukoencephalopathy (PML) or progressive multifocal leukoencephalopathy-immune reconstitution inflammatory syndrome (PML-IRIS) in a subject, the method comprising:
   providing a VP1 protein of polyoma virus JC (JCV),
   administering the VP1 protein of JCV to the subject, and
   administering an TLR-7 agonist or an TLR-8 agonist,
   thereby treating progressive multifocal leukoencephalopathy (PML) or progressive multifocal leukoencephalopathy-immune reconstitution inflammatory syndrome (PML-IRIS) in the subject.

2. The method as recited in claim 1, wherein only the TLR-7 agonist is administered.

3. The method as recited in claim 1, further comprising: administering imiquimod.

4. The method as recited in claim 1, further comprising: administering an adjuvant selected from the group consisting of MF59, aluminium hydroxide, calcium phosphate gel, lipopolysaccharides, oligonucleotide sequences with CpG motifs, stearyl tyrosine, DTP- GDP, DTP-DPP, threonyl-MDP, 7-allyl-8-oxoguanosine, glycolipid bay R1005, multi-antigen peptide system, polymerized haptenic peptides, bacterial extracts, and vit-A.

5. The method as recited in claim 1, wherein the subject has a congenital immunodeficiency, an acquired immunodeficiency resulting from a disease or pathological condition, or an acquired immunodeficiency resulting from a therapeutic intervention.

6. The method as recited in claim 5, further comprising: treating with an immunosuppressive antibody.

7. The method as recited in claim 6, wherein the immunosuppressive antibody is selected from the group consisting of natalizumab, efalizumab, rituximab, ocrelizumab and alemtuzumab.

8. The method as recited in claim 5, wherein the subject is afflicted with an autoimmune disease.

9. The method as recited in claim 8, wherein the autoimmune disease is multiple sclerosis.

10. The method as recited in claim 9, wherein the subject is to be treated with the antibody natalizumab.

11. The method as recited in claim 5, wherein the subject has a congenital immunodeficiency selected from the group consisting of idiopathic CD4+ lymphopenia and Hyper-IgE-Syndrome.

12. The method as recited in claim 5, wherein the subject has an acquired immunodeficiency resulting from a disease or pathological condition selected from the group consisting of AIDS, leukemia, lymphoma, multiple myeloma, infection with hepatitis virus B, and infection with hepatitis C.

13. The method as recited in claim 5, wherein the subject has an acquired immunodeficiency resulting from a therapeutic intervention, wherein the therapeutic intervention is selected from the group consisting of chemotherapy, radiation and immunosuppressive treatment.

* * * * *